United States Patent
Kaufman et al.

(10) Patent No.: US 7,119,328 B2
(45) Date of Patent: Oct. 10, 2006

(54) SYSTEM FOR DMS PEAK RESOLUTION

(75) Inventors: Lawrence A. Kaufman, Waltham, MA (US); Raanan A. Miller, Chestnut Hill, MA (US); Erkinjon G. Nazarov, Lexington, MA (US); Evgeny Krylov, Las Cruces, NM (US); Gary A. Eiceman, Las Cruces, NM (US)

(73) Assignee: Sionex Corporation, Bedford, MA (US)

( * ) Notice: Subject to any disclaimer, the term of this patent is extended or adjusted under 35 U.S.C. 154(b) by 69 days.

(21) Appl. No.: 10/738,967

(22) Filed: Dec. 17, 2003

(65) Prior Publication Data

US 2005/0040330 A1 Feb. 24, 2005

Related U.S. Application Data

(63) Continuation-in-part of application No. 10/187,464, filed on Jun. 28, 2002, now Pat. No. 7,045,776, which is a continuation-in-part of application No. 09/896,536, filed on Jun. 30, 2001, now abandoned.

(60) Provisional application No. 60/351,043, filed on Jan. 23, 2002, provisional application No. 60/342,588, filed on Dec. 20, 2001, provisional application No. 60/340,904, filed on Dec. 12, 2001, provisional application No. 60/334,670, filed on Nov. 15, 2001, provisional application No. 60/340,894, filed on Oct. 30, 2001.

(51) Int. Cl.
*B01D 59/44* (2006.01)
*H01J 49/00* (2006.01)
*H01J 49/44* (2006.01)

(52) U.S. Cl. ............. 250/281; 250/282; 250/286; 250/287; 250/288

(58) Field of Classification Search ............. 250/281
See application file for complete search history.

(56) References Cited

U.S. PATENT DOCUMENTS

| 2,615,135 A | 10/1952 | Glenn |
| 3,511,986 A | 5/1970 | Llewellyn |
| 3,621,240 A | 11/1971 | Cohen et al. |
| 3,931,589 A | 1/1976 | Aisenberg et al. |
| 4,025,818 A | 5/1977 | Giguere et al. |
| 4,201,921 A | 5/1980 | McCorkle |
| 4,931,640 A | 6/1990 | Marshall et al. |
| 5,019,706 A | 5/1991 | Allenmann et al. |

(Continued)

FOREIGN PATENT DOCUMENTS

RU 966583 10/1982

(Continued)

OTHER PUBLICATIONS

"A Micromachined Field Driven Radio Frequency-Ion Mobility Spectrometer for Trace Level Chemical Detection ," A Draper Laboratory Proposal Against the "Advanced Cross-Enterprise Technology Development for NASA Missions," Solicitation, NASA NRA 99-OSS-05.

(Continued)

*Primary Examiner*—Frank G. Font
*Assistant Examiner*—Mary El-Shammaa
(74) *Attorney, Agent, or Firm*—Fish & Neave IP Group Ropes & Gray LLP

(57) ABSTRACT

An apparatus for identification of chemical species by measurement of mobility as a function of high electric field and for generating unique compound-dependent signatures based on ion mobility at a plurality of peak RF voltages for a given compensation. The resulting detection data is compared against a library of data in order to identify a detected chemical species.

6 Claims, 29 Drawing Sheets

U.S. PATENT DOCUMENTS

| | | | |
|---|---|---|---|
| 5,420,424 A | 5/1995 | Carnahan et al. | |
| 5,455,417 A | 10/1995 | Sacristan | |
| 5,536,939 A | 7/1996 | Freidhoff et al. | |
| 5,654,544 A | 8/1997 | Dresch | |
| 5,723,861 A | 3/1998 | Carnahan et al. | |
| 5,763,876 A | 6/1998 | Pertinarides et al. | |
| 5,789,745 A | 8/1998 | Martin et al. | |
| 5,801,379 A | 9/1998 | Kouznetsov | |
| 5,834,771 A | 11/1998 | Yoon et al. | |
| 5,838,003 A | 11/1998 | Bertsch et al. | |
| 5,869,344 A * | 2/1999 | Linforth et al. | 436/173 |
| 5,965,882 A | 10/1999 | Megerle et al. | |
| 6,066,848 A | 5/2000 | Kassel et al. | |
| 6,107,624 A | 8/2000 | Doring et al. | |
| 6,124,592 A * | 9/2000 | Spangler | 250/287 |
| 6,200,539 B1 * | 3/2001 | Sherman et al. | 216/67 |
| 6,323,482 B1 | 11/2001 | Clemmer et al. | |
| 6,495,823 B1 * | 12/2002 | Miller et al. | 250/286 |
| 6,504,149 B1 | 1/2003 | Guevremont et al. | |
| 6,512,224 B1 | 1/2003 | Miller et al. | |
| 6,512,226 B1 * | 1/2003 | Loboda et al. | 250/292 |
| 6,618,712 B1 * | 9/2003 | Parker et al. | 706/15 |
| 6,639,212 B1 | 10/2003 | Guevremont | |
| 6,653,627 B1 | 11/2003 | Guevremont | |
| 6,690,004 B1 | 2/2004 | Miller et al. | |
| 6,703,609 B1 | 3/2004 | Guevremont | |
| 6,713,758 B1 | 3/2004 | Guevremont | |
| 6,753,522 B1 | 6/2004 | Guevremont | |
| 6,770,875 B1 | 8/2004 | Guevremont | |
| 6,774,360 B1 | 8/2004 | Guevremont | |
| 6,787,765 B1 | 9/2004 | Guevremont | |
| 6,799,355 B1 | 10/2004 | Guevremont | |
| 6,806,466 B1 | 10/2004 | Guevremont | |
| 2001/0030285 A1 | 10/2001 | Miller et al. | |
| 2002/0070338 A1 | 6/2002 | Loboda | |
| 2002/0134932 A1 | 9/2002 | Guevremont et al. | |
| 2003/0020012 A1 | 1/2003 | Guevremont et al. | |
| 2003/0038235 A1 | 2/2003 | Guevremont et al. | |
| 2003/0052263 A1 * | 3/2003 | Kaufman et al. | 250/281 |
| 2003/0089847 A1 * | 5/2003 | Guevremont et al. | 250/282 |
| 2003/0132380 A1 | 7/2003 | Miller et al. | |
| 2004/0094704 A1 | 5/2004 | Miller et al. | |

FOREIGN PATENT DOCUMENTS

| | | |
|---|---|---|
| RU | 1412447 A1 | 6/1998 |
| RU | 1485808 | 10/1998 |
| SU | 1337934 A2 | 9/1987 |
| SU | 1627984 A2 | 7/1988 |
| WO | WO 00/08454 | 2/2000 |
| WO | WO 00/08455 | 2/2000 |
| WO | WO 00/08456 | 2/2000 |
| WO | WO 00/08457 | 2/2000 |
| WO | WO 01/08197 A1 | 2/2001 |
| WO | WO 01/22049 A2 | 3/2001 |
| WO | WO 01/35441 A1 | 5/2001 |
| WO | WO 01/69217 A2 | 9/2001 |
| WO | WO 01/69220 A2 | 9/2001 |
| WO | WO 01/69647 A2 | 9/2001 |
| WO | WO 02/071053 A | 9/2002 |

OTHER PUBLICATIONS

Barnett, D.A. et al., "Isotope Separation Using High-Field Asymmetric Waveform Ion Mobility Spectrometry," Nuclear Instruments & Methods in Physics Research (2000), pp. 179-185, 450(1).

Buryakov, I.A. et al., "A New Method of Separation of Multi-Atomic Ions by Mobility at Atmospheric Pressure Using a High-Frequency Amplitude-Asymmetric Strong Electric Field," International Journal of Mass Spectometry and Ion Processes (1993), pp. 143-148, 128.

Buryakov, I.A. et al., "Sepatation Ions According to Mobility in a Strong ac electric Field,", Sov. Tech. Phs. Lett. (1991), pp. 446-447, 17(6).

Buyrykov, I.A. et al., Device and Method For Gas Electrophoresis, Chemical Analysis fo Environment, edit. Prof. V.V. Malakhov, Novosibirsk; Nauka (1991), pp. 113-127.

Carnahan, B. et al., "Field Ion Spectrometry—A New Analytical Technology for Trace Gas Analysis," ISA, (1996), pp. 87-96, 51(1).

Carnahan, B. et al., "Field Ion Spectrometry—A New Technology for Cocaine and Heroin Detection," SPIE, (1997), pp. 106-119, 2937.

Eiceman, G.A., et al., "Miniature radio-frequency mobility analyzer as a gas chromatographic detector for oxygen-containing volatile organic compounds, pheromones, and other insect attractants," J. Chromatography, (2001), pp. 205-217, 917.

Guevremont, R. and Purves, R., "High Field Asymmetric Waveform Ion Mobility Spectometry-Mass Spectrometry: An Investigation of Leucine Enkephalin Ions Produced by Electrospray Ionization," J. Am. Soc. Mass. Spectrom, (1999), pp. 492-501, 10.

Guevremont, R. et al., "Calculation of Ion Mobilities From Electrospray Ionization High Field Asymmetric Waveform Ion Mobility Spectrometry Mass Spectrometry," Journal of Chemical Physics, (2001), pp. 10270-10277, 114(23).

Guevremont, R. et al., "Atmospheric Pressure In Focusing in a High-Field Asymmetric Waveform Ion Mobility Spectrometer," Review of Scientific Instruments, (1999), pp. 1370-1383, 70(2).

Handy, Russell et al., "Determination of nanomlar levels of perchlorate in water by ESI-FAIMS-MS," JAAS (2000), pp. 907-911, 15.

Krylov, E.V., "A Method of Reducing Diffusion Losses in a Drift Spectrometer," Technical Physics, (1999), pp. 113-116, 4d(1).

Krylov, E.V., "Pulses of Special Shapes Formed on a Capacitive Load," Instruments and Experimental Techniques, (1997), pp. 628, 40(5).

Miller, R.A. et al., "A MEMS Radio-Frequency Ion Mobility Spectrometer for Chemical Agent Detection," (Jun. 2000) Proceedings of the 2000 Solid State Sensors and Actuators Workshop, Hilton Head, SC.

Miller, R.A. et al., "A MEMS radio-frequency ion mobility spectrometer for chemical vapor detection," Sensors and Actuators, (2001), pp. 301-312, A91.

Miller, R.A. et al., "A Novel Micromachined High-Field Asymmetric Waveform-Ion Mobility Spectrometer," Sensors and Actuators B, (2000) pp. 300-306, B67 (3).

Pilzecker, P. et al., "On-Site Investigations of Gas Insulated Substations Using Ion Mobility Spectrometry for Remote Sensing of SF6 Decomposition," IEEE, (2000), pp. 400-403.

Riegner, D.E. et al., "Qualitative Evaluation of Field Ion Spectrometry for Chemical Warfare Agent Detection," Proceedings of the ASMS Conference on Mass Spectrometry and Allied Topics (Jun. 1997), pp. 473A-473B.

Schneider, A. et al., High Sensitivity GC-FIS for Simultaneous Detection of Chemical Warfare Agents, Mine Safety Appliances Co., Pittsburgh, PA, USA, (2000), AT-Process, pp. 124-136, 5(3,4), CODEN: APJCFR ISSN: 1077-419X.

Vaidyanathan, S., et al., "Flow-Injection Electrospray Ionization Mass Spectrometry of Crude Cell Extracts for High-Throughput Bacterial Identification," J. Am. Soc. Mass. Spectrom., (2002) pp. 118-128, 13.

Krylov, E.V., "Comparison of the Planar and Coaxial Field Asymmetrical Waveform Ion Mobility Spectrometer (FAIMS)," International Journal of Mass Spectrometry, 225, (2003) pp. 39-51.

* cited by examiner

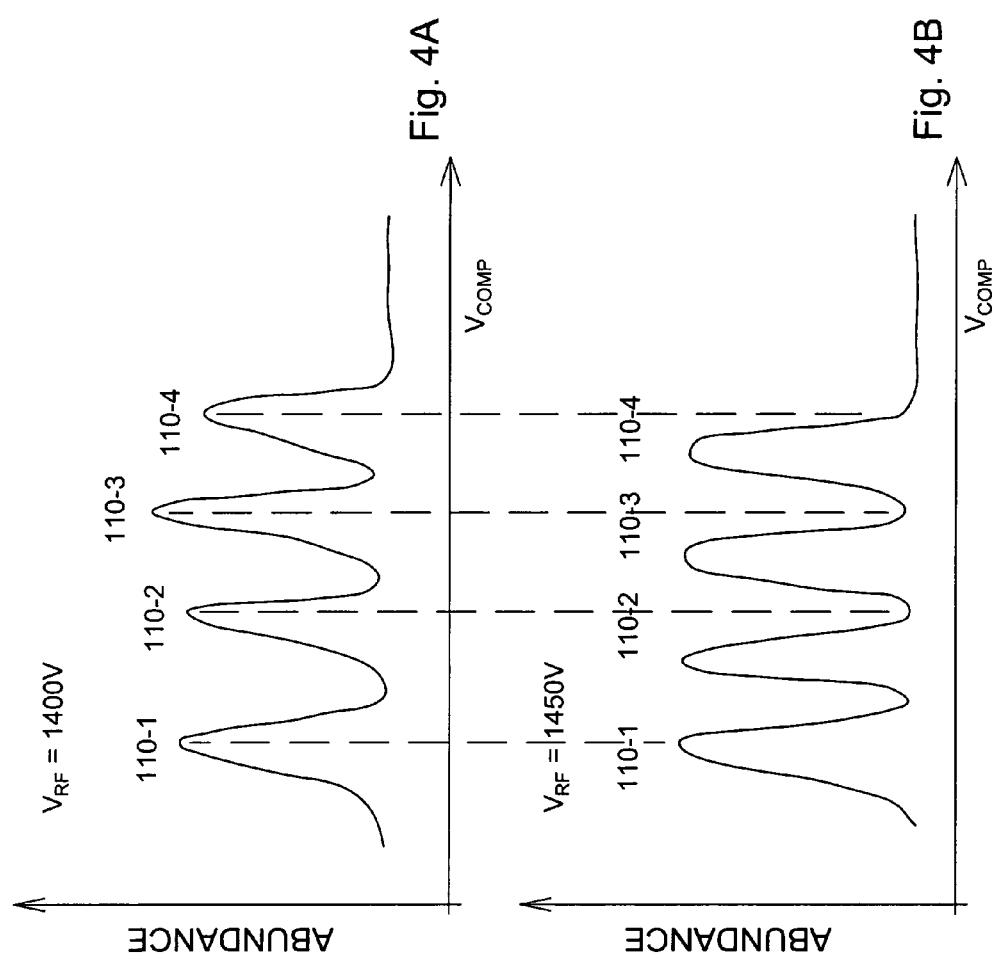

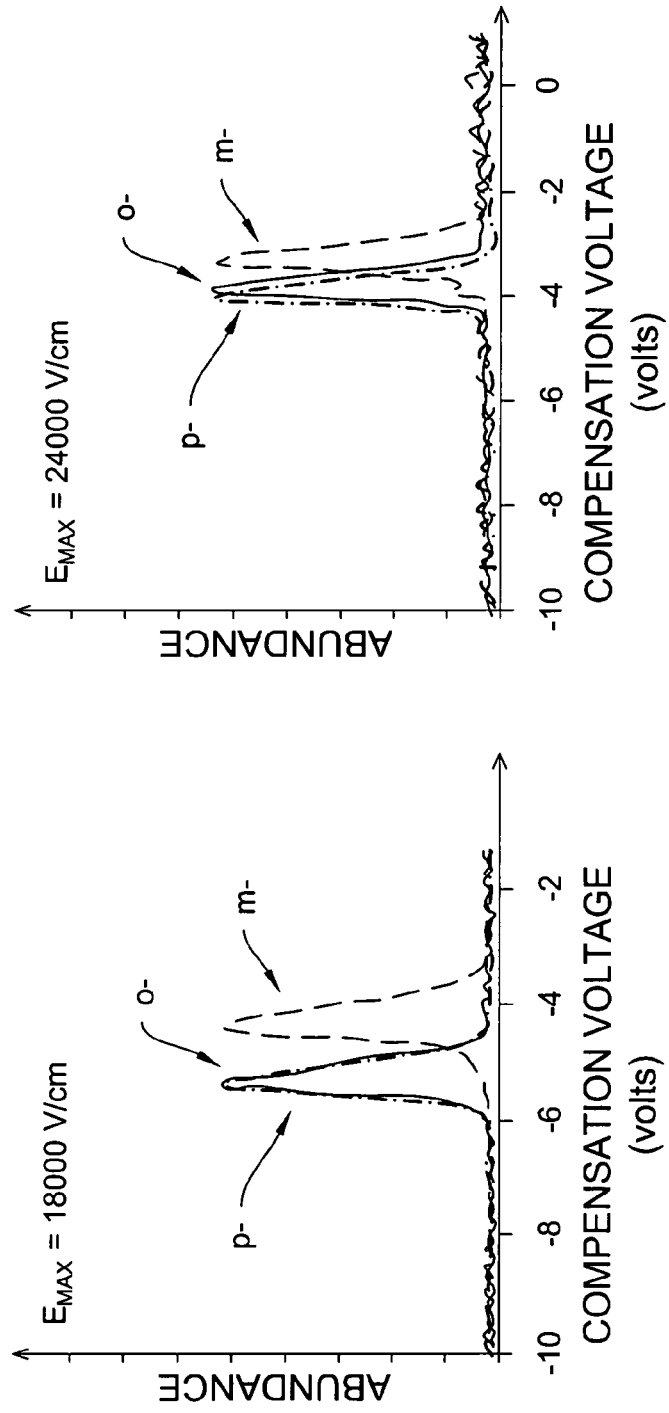

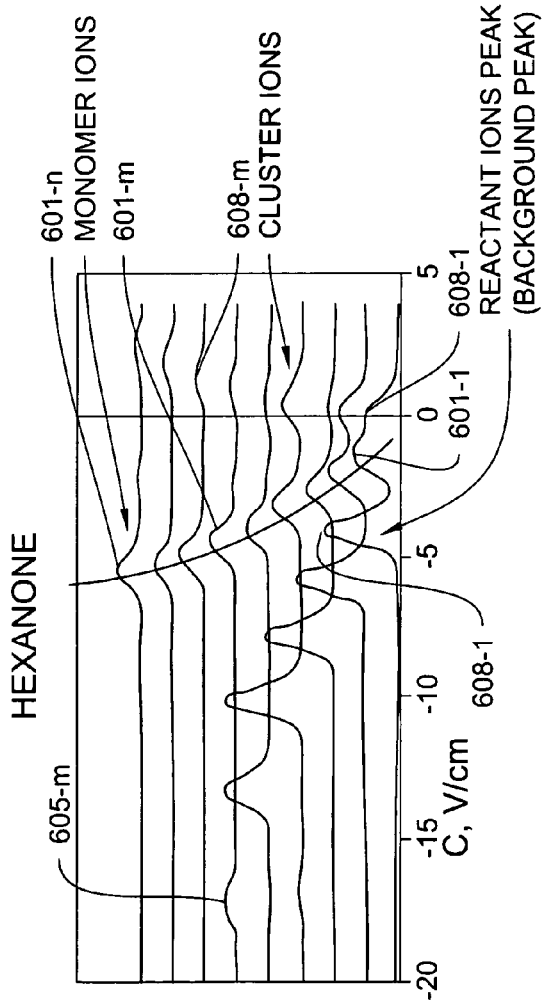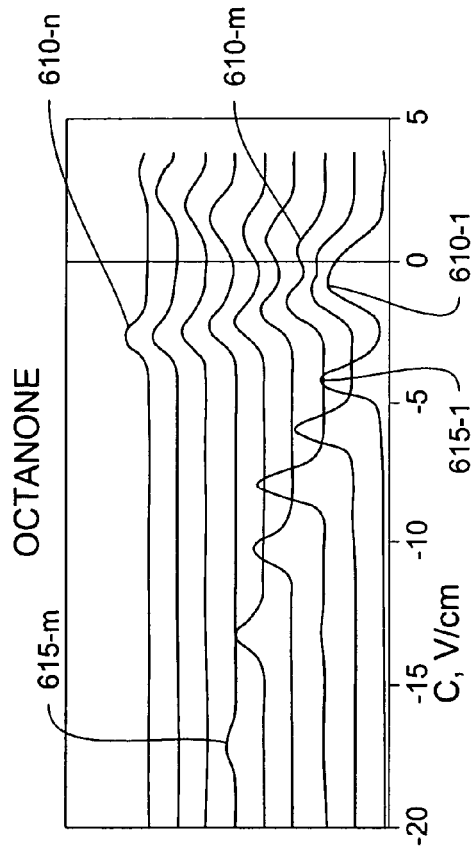
Fig. 6A
Fig. 6B

TABLE 1: VALUES FOR ALPHA PARAMETERS FOR IONS OF KETONES

Protonated Monomer

| | Acetone | Butanone | Pentanone | Hexanone | Heptanone | Octanone | Nonanone | Decanone |
|---|---|---|---|---|---|---|---|---|
| Formula | $C_3H_6OH^+$ | $C_4H_8OH^+$ | $C_5H_{10}OH^+$ | $C_6H_{12}OH^+$ | $C_7H_{14}OH^+$ | $C_8H_{16}OH^+$ | $C_9H_{18}OH^+$ | $C_{10}H_{20}OH^+$ |
| m/z (amu) | 59 | 73 | 87 | 101 | 115 | 129 | 143 | 157 |
| $\alpha_2$ [% - Td] | $3.14 \times 10^{-3}$ | $2.7 \times 10^{-3}$ | $2.1 \times 10^{-3}$ | $1.7 \times 10^{-3}$ | $1.2 \times 10^{-3}$ | $8.4 \times 10^{-4}$ | $6.5 \times 10^{-4}$ | $4.6 \times 10^{-4}$ |
| $\alpha_4$ [% - Td] | $-9.54 \times 10^{-8}$ | $-1.4 \times 10^{-7}$ | $-1.2 \times 10^{-7}$ | $-1.1 \times 10^{-7}$ | $-8.8 \times 10^{-8}$ | $-6.9 \times 10^{-8}$ | $-6.6 \times 10^{-8}$ | $-5.2 \times 10^{-8}$ |

Proton Bound Dimer

| | Acetone | Butanone | Pentanone | Hexanone | Heptanone | Octanone | Nonanone | Decanone |
|---|---|---|---|---|---|---|---|---|
| Formula | $(C_3H_6O)_2H^+$ | $(C_4H_8O)_2H^+$ | $(C_5H_{10}O)_2H^+$ | $(C_6H_{12}O)_2H^+$ | $(C_7H_{14}O)_2H^+$ | $(C_8H_{16}O)_2H^+$ | $(C_9H_{18}O)_2H^+$ | $(C_{10}H_{20}O)_2H^+$ |
| m/z (amu) | 117 | 145 | 173 | 201 | 229 | 257 | 285 | 303 |
| $\alpha_2$ [% - Td] | $1.34 \times 10^{-3}$ | $8.0 \times 10^{-4}$ | $1.9 \times 10^{-4}$ | $1.9 \times 10^{-4}$ | $2.5 \times 10^{-5}$ | $-3.5 \times 10^{-5}$ | $-2.2 \times 10^{-4}$ | $-3.5 \times 10^{-4}$ |
| $\alpha_4$ [% - Td] | $-1.77 \times 10^{-7}$ | $-1.2 \times 10^{-7}$ | $-6.0 \times 10^{-8}$ | $-8.0 \times 10^{-8}$ | $-6.8 \times 10^{-8}$ | $-6.9 \times 10^{-8}$ | $-4.8 \times 10^{-8}$ | $-3.2 \times 10^{-8}$ |

Fig. 8C

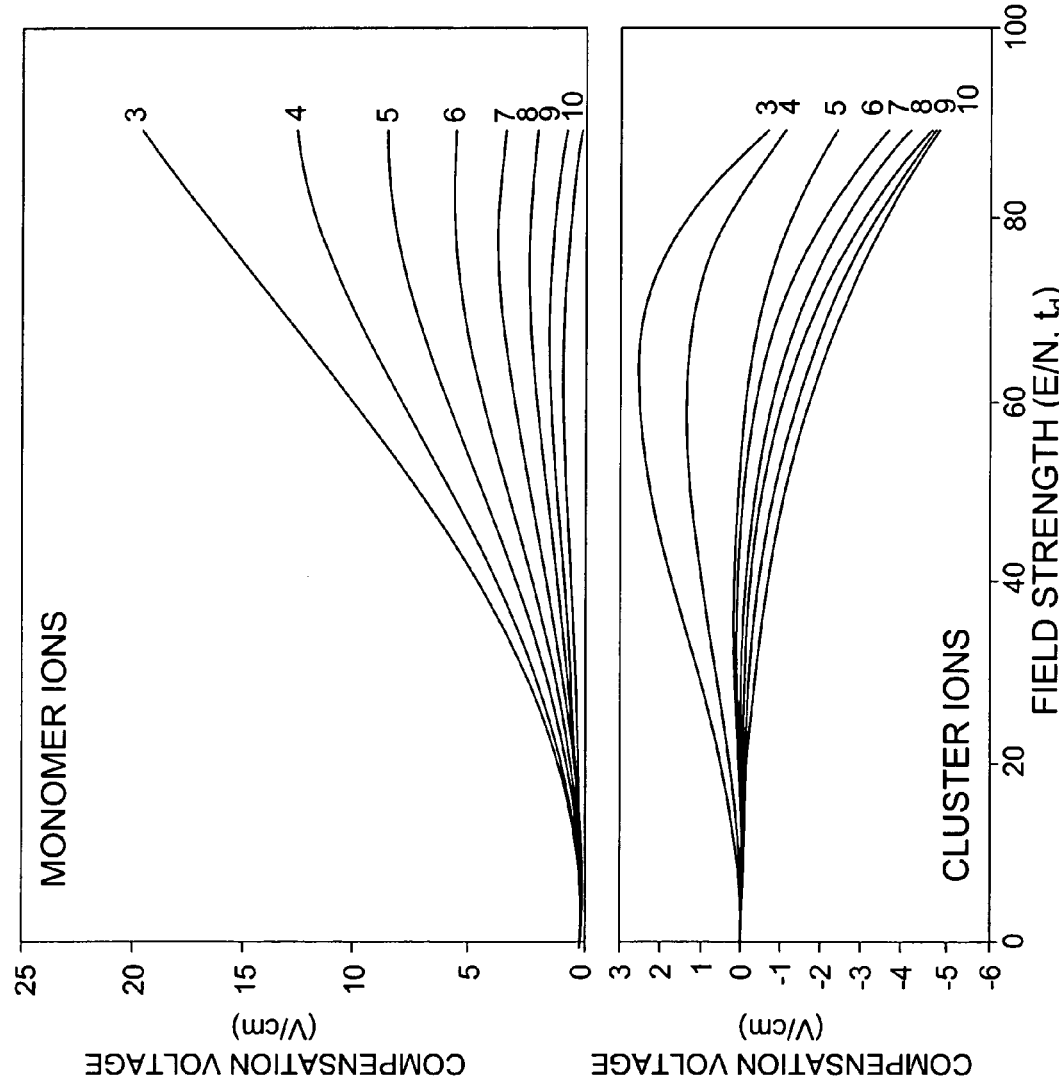

| COMPOUND ID | $V_{C11}, a_{11}$ | ... | $V_{C1n}, a_{1n}$ | ... | $V_{Cm1}, a_{m1}$ | $V_{Cm2}, a_{m2}$ | $V_{Cmn}, a_{mn}$ |
|---|---|---|---|---|---|---|---|
| $V_{DISP1}$ | | ... | | ... | | | |
| $V_{DISP\ m}$ | | | | | | | |
| $V_{DISP\ m2}$ | | | | | | | |
| $V_{DISP\ mn}$ | | | | | | | |

| COMPOUND ID | | | | |
|---|---|---|---|---|
| $V_{RF1}$ | $V_{C11}, A_{11}, L_{11}$ | $V_{C12}, A_{12}, L_{12}$ | ••••• | $V_{C1n}, A_{1n}, L_{1n}$ |
| $V_{RF2}$ | $V_{C21}, A_{21}, L_{21}$ | $V_{C22}, A_{22}, L_{22}$ | ••••• | $V_{C2n}, A_{2n}, L_{2n}$ |
| | ••••• | ••••• | | ••••• |
| $V_{RFm}$ | $V_{Cm1}, A_{m1}, L_{m1}$ | $V_{Cm2}, A_{m2}, L_{m2}$ | | $V_{Cmn}, A_{mn}, L_{mn}$ |
| $V_{FRAG}$ | | | | |

$L = \{monomer, cluster, RIP\}$

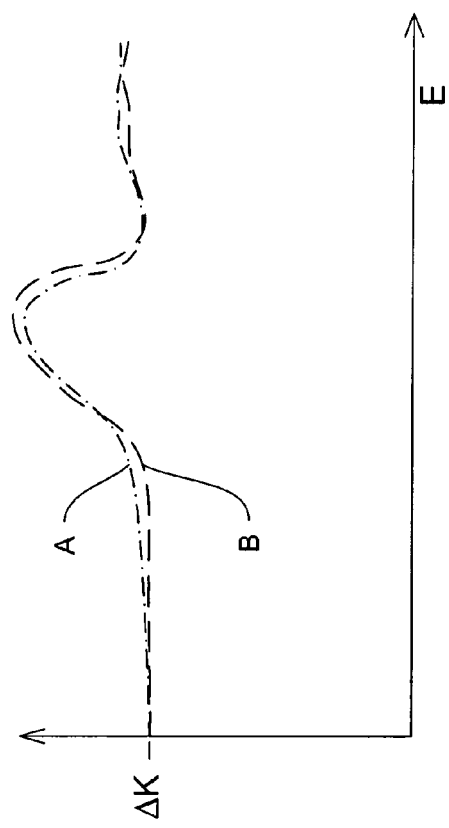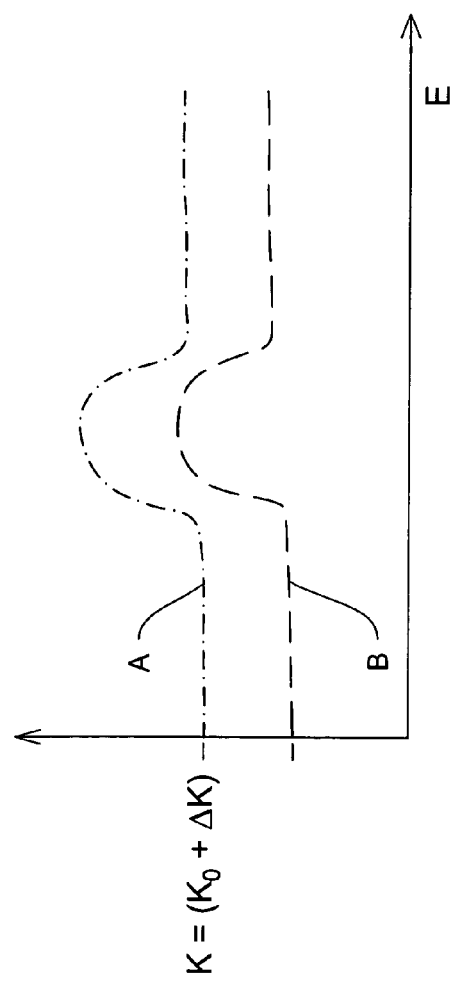

SYSTEM FOR DMS PEAK RESOLUTION

RELATED APPLICATION(S)

This application is a continuation-in-part of U.S. application Ser. No. 10/187,464, filed Jun. 28, 2002 now U.S Pat. No. 7,045,776 entitled "System For Collection Of Data And Identification Of Unknown Ion Species In An Electric Field," which is a continuation-in-part of U.S. application Ser. No. 09/896,536 filed Jun. 30, 2001 now abandoned entitled "Apparatus For Simultaneous Identification Of Multiple Chemical Compounds;" and claims the benefit of U.S. Provisional Application No. 60/340,894 filed Oct. 30, 2001 entitled "Compound Identification By Mobility Dependence On Electric Field," U.S. Provisional Application No. 60/334, 670, filed Nov. 15, 2001 now abandoned entitled "System For Ion Mobility And Polarity Discrimination And Identification Of Chemical Compounds;" U.S. Provisional Application No. 60/340,904, filed Dec. 12, 2001 entitled "System For Ion Mobility And Polarity Discrimination And Identification Of Chemical Compounds;" U.S. Provisional Application No. 60/342,588 filed Dec. 20, 2001 entitled "Field Dependence Of Mobilities For Gas Phase Protonated Monomers And Proton Bound Dimers Of Ketones By Planar Field Asymmetric Waveform Ion Mobility Spectrometer (PFAIMS);" and U.S. Provisional Application No. 60/351, 043 filed Jan. 23, 2002 entitled "Method And Apparatus For FAIMS Detection Of SF6," all of which are incorporated herein by reference.

BACKGROUND OF THE INVENTION

The present invention relates generally to identification of unknown members of a sample by mobility characteristics, and more particularly to devices that analyze compounds via high field asymmetric waveform ion mobility spectrometry.

There are a number of different circumstances in which it is desirable to perform a chemical analysis to identify compounds in a sample. Such samples may be taken directly from the environment or they may be provided by front end specialized devices to separate or prepare compounds before analysis. Unfortunately, recent events have seen members of the general public exposed to dangerous chemical compounds in situations where previously no thought was given to such exposure. There exists, therefore, a demand for low cost, accurate, easy to use, and reliable devices capable of detecting the chemical makeup of a sample.

One class of known chemical analysis instruments are mass spectrometers. Mass spectrometers are generally recognized as being the most accurate type of detectors for compound identification, given that they can generate a fingerprint pattern for even fragment ions. However, mass spectrometers are quite expensive, easily exceeding a cost of $100,000 or more and are physically large enough to become difficult to deploy everywhere the public might be exposed to dangerous chemicals. Mass spectrometers also suffer from other shortcomings such as the need to operate at relatively low pressures, resulting in complex support systems. They also need a highly trained operator to tend to and interpret the results. Accordingly, mass spectrometers are generally difficult to use outside of laboratories.

A class of chemical analysis instruments more suitable for field operation is known as are known as Field Asymmetric Ion Mobility Spectrometers (FAIMS), also known as Radio Frequency Ion Mobility Spectrometers (RFIMS), and Differential Mobility Spectrometers (DMS), among other names. This type of spectrometer subjects an ionized gas sample to a varying high-low asymmetric electric field and filters ions based on their field mobility.

The gas sample flows through a field which allows only selected ion species to pass through, according to the compensation voltage, and specifically only those ions that exhibit particular mobility responses to the field. An ion detector then collects detection intensity data for the detected ions. The intensity data exhibit attributes such as "peaks." These peaks are interpreted according to the compensation voltage at which a species of ion is able to pass through an asymmetric field of set field parameters.

A typical FAIMS device includes a pair of electrodes in a drift tube. An asymmetric field is applied to the electrodes across the ion flow path. The asymmetric RF field, as shown in FIG. 1A, alternates between a high or "peak" field strength and a low field strength. The field varies with a particular time period, t, (frequency) and duty cycle d. Field strength, E, varies as the applied voltage V and size of the gap between electrodes. Ions will pass through the gap between the electrodes only when their net transverse displacement per period of the asymmetric field is zero; in contrast, ions that undergo a net displacement will eventually undergo collisional neutralization on one of the electrodes. In a given Radio Frequency (RF) asymmetric field, a displaced ion can be restored to the center of the gap (i.e. compensated, with no net displacement for that ion) when a low strength DC electric field (the compensation voltage, Vcomp) is superimposed on the RF. Ions with differing displacement (owing to characteristic dependence of mobility in the high field condition) can be passed through the gap at compensation voltages characteristic of a particular ion and this is accomplished by applying various strengths of Vcomp. In this case, this system can function as continuous ion filter; or a scan of Vcomp will allow complete measure of ion species in the analyzer. The recorded image of the spectral scan of the sample is sometimes referred to as a "mobility scan" or as an "ionogram").

Examples of mobility scans based on the output from a FAIMS device are shown in FIGS. 1B-1 and 1B-2. The compounds analyzed here consisted of acetone and an isomer of xylene (o-xylene). In the first case (FIG. 1B-1) a single compound, acetone, was independently applied to the FAIMS analyzer. The illustrated plot is typical of the observed response of the FAIMS device, with an intensity of detected ions dependent on the compensation voltage (Vcomp). For example, the acetone sample exhibited a peak intensity response at a compensation voltage of approximately −2 volts.

FIG. 1B-2 illustrates the results when analyzing a mixture of the two compounds, here, acetone and o-xylene. The combined response shows two peaks in approximately the same region as for the independent case. The compounds in the mixture can therefore be detected by comparing the response against the library, for example, of stored known responses for independently analyzed compounds, or libraries of mixtures. Thus, the independently analyzed compounds shown in FIG. 1B-1 can be stored in a computer system, and when compound responses such as that in FIG. 1B-2 are observed, the relative locations of the peaks can be compared against the stored responses in the library to determine the constitution of the mixture.

A problem occurs, however, especially with FAIMS devices, in that relatively complex samples can be very difficult to detect. First of all, the peaks as seen in the typical FAIMS spectra are generally broad in width. Therefore, compounds having similar peak compensation voltages may therefore be difficult to separate from one another. Indeed, there may be particular conditions where two different chemicals actually exhibit the same compensation voltage at a given maximum intensity for the applied asymmetric RF voltage (referred to here as peak RF voltage). In such a case, it is not possible to resolve between two different chemicals at all. Another problem may occur when two or more chemical species have the same or almost the same mobility. This is most likely to happen in the low electric field regime where most existing ion mobility spectrometer systems operate. Therefore, if two or more chemical species have the same or almost the same mobility, then their spectroscopic peaks will overlap, and identification and quantification of individual species will be difficult or impossible.

A specific RF level and compensation voltage will permit only a particular species of ion (according to mobility) to pass through the filter to the detector. By noting the RF level and compensation voltage and the corresponding detected signal, various ion species can be identified, as well as their relative concentrations (as seen in the peak characteristics).

Consider a plot of mobility dependence on electric field, as shown in FIG. 1C. This figure mobility versus electric field strength for three examples of ions, with field dependent mobility (expressed as the coefficient of high field mobility, a) shown for species at greater, equal to and less than zero. The velocity of an ion can be measured in an electric field, E, low enough so that velocity, V, is proportional to the electrical field as V=KE through a coefficient, K, called the coefficient of mobility. K can be shown to be theoretically related to the ion species and gas molecular interaction properties. This coefficient of mobility is considered to be a unique parameter that enables the identification of different ion species and is determined by, ion properties such as charge, size, and mass as well as the collision frequency and energy obtained by ions between collisions.

When the ratio of E/N is small, K is constant in value, but at increasing E/N values, the coefficient of mobility begins to vary. The effect of the electric field can be expressed approximately as $$K(E)=K(0)[1+\alpha(E)]$$

where $K(0)$ is a low voltage coefficient of mobility, and $\alpha$ is a specific parameter showing the electric field dependence of mobility for a specific ion.

Thus, as exhibited in FIG. 1C, at relatively low electric field strengths, of say less than approximately 8,000 volts per centimeter (V/cm), multiple ions may have the same mobility. However, as the electric field strengths increase, the different species diverge in their response such that their mobility varies as a function of the applied electric field. This is a clear expression of the fact that ion mobility is independent of applied electric field at relatively low field strengths but is field-dependent at higher applied field strengths.

FIG. 1B demonstrates that each species can have a unique behavior in high fields according to its mobility characteristics. The ions passing through the filter are detected downstream. The detection signal intensity can be plotted, resulting in display of a characteristic detection peak for a given RF and Vcomp. Peak intensity, location, and shape are typically used for species identification.

However, a problem occurs, especially with FAIMS devices, in that relatively complex samples can be very difficult to discriminate. First of all, the peaks as seen in the typical FAIMS spectra are generally broad in width. Therefore, compounds having similar peak compensation voltages may be difficult to separate from one another. Indeed, there may be particular conditions where two different chemicals actually exhibit the same peak at the same compensation voltage at a given asymmetric RF field.

For example in FIG. 1D, there are four compounds each with a unique characteristic mobility curve that expresses the mobility dependence associated with that compound at each of various peak RF values and compensation voltage levels. Four different chemical compounds are shown, including lutidine, cyclohexane, benzene, and a chemical agent simulant dimethyl-methyl-phosphonate (DMMP). Each curve shows detection peaks at the various field conditions that in total are characteristic for the compound. As shown, there is a region 100 in which the mobility curves for DMMP and cyclohexane overlap with one another. Therefore, operating in a peak RF voltage region of from approximately 2,500 to 2,650 volts, at around −6 to −8 volts compensation, one would find it impossible to discriminate between the two compounds upon a single scan. In other words, the conventional spectral scan would plot the overlapping peaks as a single peak at that field condition.

A cylindrical FAIMS device is described in U.S. Pat. No. 5,420,424, where the amplitude of the asymmetric periodic potential is in the range of about 1 to 6 Kv or 2 to 5 Kv, and preferably at about 3 Kv, depending on the ionic species of interest. After the magnitude of the asymmetric voltage has been set, the compensation voltage is held constant or scanned to provide separation of the ionic species.

Even with these improvements, ion species detection is not error free, especially with complex sample mixtures. False negatives are dangerous, and false positives can be expensive and reduce trust in the device. This can be very serious where harmful compounds are being monitored. It is also desirable to have a fast and simple apparatus to achieve such detections with improved accuracy.

SUMMARY OF THE INVENTION

The present invention is directed to a method and system for identification of unknown species of ions traveling through an asymmetric excitation field, the identification being based on the known characteristic mobility behavior of ion species under known field conditions.

Illustrative apparatus of the invention includes an ionization section, a filter section, a detection section, an identification section, and a controller section. The controller (e.g., microprocessor, laptop, etc.) may typically incorporate the identification section (lookup table, comparator, etc.).

In practice of the invention, we disclose innovations for isolating ion species of interest in a sample and positively identifying the species with a high degree of reliability. We apply techniques for improving the detection and identification processes. This process may also include separating the ions from background noise or from other ion species in the sample.

In one significant aspect, the present invention intentionally controls and uses changes of the filter field (i.e., changes in "field conditions") for better revealing and isolating ion species in the sample. The ionization and filter sections may assume many different physical forms.

As ions are passed through the filter, they deposit charges at a detector. The intensity of the detection is then recorded against the compensation voltage (Vcomp) for a set RF condition (Vrf). Spectral peaks may also be determined while Vcomp is scanned through a range.

The present invention then takes this process further. Specifically, we have identified stratagem for improving species discrimination by intentionally controlling field conditions in a manner that results in improved isolation of ion species. In one embodiment, this involves detecting ion species behavior in response to at least two different applied RF field strengths, and thus at two different sets of field conditions. At each ion species detection we associate the applied compensation and RF with the detection signal and match or correlate this with known data to identify the detected ion species.

Several methods of adjusting field conditions may be used, including adjusting field strength, frequency, aspects of the waveform asymmetry, pulse shape, duty cycle, and the like, to effect meaningful changes in field conditions that affect ion mobility. These alternatives are selected for the ability they provide in separating and isolating ion species in the sample. This assumes that the ion species are sensitive to such changes. As long as there is a desirable effect on the mobility behavior of the ions in the field then we can make use of this control. In all events these controls are directed to causing one species to behave differently from another species in the field so that a more refined or better defined set of ions can be passed to the detector.

Therefore, for purposes of this invention, we define "field conditions" and "set of field conditions" as any combination of compensation and RF established in the gap between the filter electrodes as may affect ion mobility. Field conditions are considered to be different when attributes of the RF or compensation have been changed, whether this takes the form of adjustment in frequency, intensity, asymmetry, periodicity, pulse shape or similar variables. Nevertheless, we can control the field conditions and the energy in the field in a manner that has differential effect upon ion mobility in the field. We use this differential effect in controlling ion filtering. In a preferred embodiment, "field conditions" also will be understood to take into account various other aspects such as temperature, flow rate, pressure, and flow volume in the filter, as well as the nature of the carrier gas, if any.

Field conditions can be controlled by several techniques in practice of the invention. For example, frequency has an effect on the 'selectivity' (width) of the output scanned peaks. This can be implemented by changing the value of a fixed operating frequency or by dynamic frequency modulation where a range of frequencies could be scanned, for example. Control of pulse shape, i.e., square, triangular, sinusoidal, ramp, also may be adjusted, where shape may be used to affect response of the ion in the field in a known manner. Magnetic fields may also be used to control flow of ions according to known response characteristics.

The compensation voltage Vcomp may be a separate DC voltage or it may be imposed on the RF signal Vrf, such as by varying the duty cycle. The term compensation therefore will be understood as an adjustment to the field by bias voltage or other means that enables tuning the field to pass a desired species of ion to the detector. When we run a spectral scan, we normally scan the compensation voltage through a range of values. However, varying the duty cycle or pulse width can have an effect similar to adjusting or scanning the compensation voltage. The latter can be accomplished by holding the pulse width constant while varying the frequency or by holding the frequency constant while varying the pulse width. We also can apply techniques of pulse amplitude modulation, which is yet another method for generating and adjusting the compensation. Alternatively, with a fixed pulse amplitude, compensation can be generated by varying baseline voltage. These controls can be produced with analog circuitry or can be generated digitally.

These and still other control strategies are within the spirit and scope of the invention as will appear to a person skilled in the art.

We therefore exercise our ability to control ion behavior in the electric field by control of field conditions, knowing that different ion species will pass through the filter depending upon these field conditions. In one example, we set the field strength, e.g., amplitude of the RF signal, and then adjust or shift the compensation to a level needed to detect an ion species. If we detect a peak at this set of field conditions, we take this detection data (noting detection peak and field conditions), and then compare this to a store of mobility behavior of known ion species. Upon finding a match or near match, we can make a reliable identification of the species of the detected ions.

We further exercise field control to distinguish between multiple detection data that may require further clarity. Thus at one set of field conditions some peaks may seem to overlap, but after making a field adjustment such as changing field strength or compensation, these overlapping peaks will be separated and be separately processable as will enable separate identification of the species each represents. Detections thus proceed where detection data and field conditions are correlated with stored data to make positive species identifications.

It will be appreciated by a person skilled in the art that a "reactant ion peak" (RIP) may be detected in a FAIMS device and will be associated with ions that result from ionization of the background environment in the drift tube. This background may include molecules of carrier gas that are ionized, and perhaps also water molecules that become protonated, during the ionization process. Peaks associated with detection of these ions are referred to as "reactant ion peaks" as opposed to peaks associated with detection of chemical ions of interest.

In practice of the present invention, in one example, increasing the RF field strength typically has a much more dramatic effect on the background RIP than on a sample ion species; as a result of sampling at two or more of a series of different field conditions (whether the difference is in the RF field or the compensation), the RIP peak can be shifted away from the peak for an ion species of interest.

This separation of detection data isolates the ion species of interest from the background detection data and results in a cleaner and more accurate species detection and identification. In this manner, detection accuracy is improved and false positives are reduced in practice of the invention.

Furthermore, intentionally changing or scanning across a range of field conditions can cause the peaks associated with complex or clustered compounds to shift away from peaks associated with monomers in a sample. This enable better species isolation. Furthermore, with sufficient increase in field strength, clustered compounds will even tend to decluster and resolve into identifiable constituents. Therefore, a single complex compound may be identified by its characteristic component ions or sub-clusters, again based on comparison of field conditions and detection data compared to a known data store.

In embodiments of the invention, we control ionization, such as by increasing ionization energy and fragmenting the sample into characteristic component parts. This increases specificity of the detection data. In other embodiments, we increase the RF energy in the filter section to accomplish fragmentation. This again enables component parts of a sample to be separately detected, the combination of detections enabling us to more accurately identify the ion species in the sample. Thus we can control actions in the ionization section or in the filter section to favorably impact the quality of the detection signal.

In the detector region, we note the field conditions in the filter section (as well as ionization and flow) and then we correlate this with detection intensity data. This characterizes an ion species detection of unknown type. This detection data is compared to stored detector data for known species at known filed conditions and a detection identification is made. This approach is simplified, but may be adequate for various embodiments of the invention.

However, in practice of further embodiments of the invention, we also do further processing of the detection signal using techniques such as by evaluating peak spectral energy, generating mobility curves, curve matching, and the like. This enables a more definitive detection process.

In one practice of the invention, a detection is made of an ion species at at least two field conditions. Identification is made by collecting multiple detection data representing a signature of the detected ion species in these field conditions, and then by comparing this signature data to a store of known species signatures. The ion species to be identified may be traveling alone or in a group of ions of same or differing characteristic mobility behavior. Nevertheless, we can achieve species-specific isolation and identification.

In yet another embodiment, a FAIMS device operates simultaneously in both positive ion detection mode ("positive mode" or "positive ion mode") and negative ion detection mode ("negative mode" or "negative ion mode") for complete real-time sample analysis. Alternatively, two separate FAIMS devices may operate in tandem, one in each mode, and detection results can be processed either seriatim or simultaneously and combined for complete real-time sample analysis.

A preferred method and apparatus detects multiple species simultaneously based on both ion mobility and ion polarity. A preferred method and apparatus of the invention includes a FAIMS spectrometer applied to filtering and simultaneous transport and detection of positive and negative ion species from a sample including mercaptans and other sulfur-containing compounds, and air, methane or other gases.

In one practice of the invention, a compensated asymmetric high RF field is used to separate sulfur-containing compounds (such as mercaptans) from a hydrocarbon background (such as methane). The sample is ionized and the ions representing sulfur-containing compounds (such as mercaptans) are detected according to polarity (i.e., for the most part as negative ions). The hydrocarbons are detected according to polarity (i.e., for the most part as positive ions) in the same device. These detections may even be performed simultaneously where dual detectors are oppositely biased.

In one specific end use, the invention enables detection of trace amounts (ppm, ppb, ppt) of mercaptan in varying and even high hydrocarbon backgrounds. The device is also able to characterize the hydrocarbon gas backgrounds. A preferred practice of the invention has the ability to detect trace amounts of sulfur-containing compounds (e.g., mercaptans) in varying and even high hydrocarbon backgrounds and to characterized the hydrocarbon backgrounds in the same device simultaneously.

In this embodiment of the invention, a gas sample having sulfur-containing compounds (e.g., mercaptans) and methane (or other gases including air) are ionized and flowed through a FAIMS filter. Negative ions are detected indicative of the concentration and identity of the sulfur-containing compounds. The same test is run again and positive ions are detected indicative of the hydrocarbon gas in the sample.

These compounds are passed by the FAIMS filter based on their mobility behavior and their having similar trajectories in the presence of compensated electric filter fields. The passed ions are then further separated based on polarity, wherein, for example, mercaptans can be distinguished from a gas such as air or methane. In the negative mode, mercaptans are detected and in the positive mode, the gas (e.g., methane) is distinguished from the mercaptans. Both modes can be run simultaneously.

It will thus be appreciated that it has been found generally that samples such as hydrocarbon gas will separate into predominantly positive ion species and sulfur-containing compounds (e.g., mercaptans) will separate into predominantly negative ion species. The preferred FAIMS spectrometer is a simple and low cost device, which can perform substantive quantitative analysis of complex mixtures having sulfur-containing compounds (e.g., mercaptans) in a gas, such as hydrocarbon or air.

In practice of the invention, a single positively biased detector electrode downstream from the filter will detect the negatively charged ion stream (negative mode). A single negatively biased detector electrode downstream from the filter will detect the positively charged ion stream (positive mode). A detection signal is generated as these ions deposit their charges on a detector electrode. These detections can be correlated with the RF signal, compensation voltage and detector bias, to identify the detected ion species.

Where two detector electrodes are provided downstream, each oppositely biased, both positive and negatively charged ion species can be detected and identified. In one practice of the invention, where mercaptans were detected in hydrocarbon background, the asymmetric voltage applied to the ion filter electrodes ranged from about 900 to about 1.5 kV (high field condition), and a low voltage of about −400 to −500 V (low field condition). The frequency ranged 1–2 MHz and the high frequency had an approximate 30% duty cycle, although other operating ranges are possible. In one embodiment, the detector electrodes were biased at +5v and −5v. Now the mercaptans are detected in the negative mode and the hydrocarbon gases can be detected in the positive mode.

The above identification process, while remarkably powerful and useful, may in some applications be substantially improved and simplified by incorporation and use of $\alpha$ parameter (coefficient of high field mobility) information and $\alpha$ curves as part of positive, highly reliable, identification process using unique mobility signatures.

Furthermore, we have found that the field-dependent mobility of a species can be expressed as an $\alpha$ function. In point of fact, the coefficient of field-dependent mobility, $\alpha$, for a species is expressed as a function of the electric field. The resulting curve showing the experienced mobility or "$\alpha$" curve, is a unique signature for that species. Furthermore, this signature can be expressed in a device-independent function.

The characteristic mobility for each species can be plotted at multiple field conditions (i.e., detection intensity noted at a series of field conditions), and this and can be expressed as a unique "$\alpha$ function" that identifies the ion species uniquely.

We note that use of the field mobility dependence coefficient $\alpha$ for a single set of field conditions does not necessarily result in a unique identification, because multiple different species can happen to have the same mobility in that single set of field conditions. We have found however that obtaining multiple $\alpha$ data sets for a detected species enables us to uniquely identify that species by its computed "α curve" even when it is indistinguishable from other species in one set of field conditions.

In one practice of the invention, we use the α function to make unique identification of a specific ion species in a sample by using two closely related detection data sets (i.e., noting detection intensity at two different but close sets of field conditions). We use these related sets of field condition values as two points on a curve, and from which we generate the slope and sign of the curve. We then can associate sign and slope with each detection and can compare to stored known detection results. Thus we can identify a detected ion species (with two detections) according to its associated mobility curve. Furthermore, we have determined that this mobility curve is species specific, and we have further identified a process for making such identification device-independent. In any case, we compare detected and computed data to a store of known data to make positive identification of the species of detected ions.

The system of the present invention (which may be expressed as either method and/or apparatus) is for identification of species of unknown ions that travel through a varying excitation field. The field is characterized as having varying influence upon the mobility behavior of the species (single or plural) of ions (single or plural) traveling through the field. The identification of the detected ion(s) is based on correlating the field-dependent mobility behavior of the detected ion(s) to a store of known field-dependent mobility behavior(s) of at least one known species.

We can scan at multiple field conditions to obtain multiple detection peaks. We can also fragment, decluster, or use dopants to control or generate additional or clarify existing detection peaks as needed. We can use these alternative to generate multiple detection data for a particular situation, and this data is processed using various evaluation strategies, such as curve/peak matching, etc., and then we do a lookup comparison for positive identification of the species of the detected ion(s). A match enables positive identification of a detected ion species in a sample.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 2 is a schematic of a preferred field asymmetric ion mobility spectrometer in practice of the present invention.

FIGS. 4A and 4B illustrate changes in peak location change in compensation in practice of the present invention.

FIGS. 5A and 5B illustrate ability to discriminate between detected ion species by changes in field conditions in practice of the present invention.

FIGS. 6A and 6B illustrate the affect of changes in field conditions, such as changes in compensation, on specific spectra, and showing divergent behavior of monomer, cluster, and reactant ion peak (RIP) detections with changes in field for hexanone and octanone in practice of the present invention.

FIG. 8C includes Table 1, which is a collection of detection data from which the curves of FIGS. 8A and 8B were generated for a group of monomer and dimers (clusters) for eight ketones in practice of the present invention.

FIGS. 9A and 9B illustrate the results of calculating normalized alpha parameter curves in practice of the present invention.

FIG. 10B shows a diagram of one possible data structure for a library of stored compound data measurement information in practice of the present invention.

FIG. 11A, 11B show spectra before and after processing according to a low-field enhanced DMS embodiment of the invention.

DETAILED DESCRIPTION OF PREFERRED EMBODIMENTS

A. A Field Asymmetric Ion Mobility Spectrometer

By way of general introduction, the present invention has particular application to high field ion mobility spectrometry and includes the recognition that improved identification or discrimination of compounds may be achieved. However, the invention may be practiced in many different field-driven and gas-driven embodiments.

One aspect of our innovation can be stated in terms of the steps of a process. Specifically, a system is used to cause species of unknown ions to travel through an excitation field. The field has a varying influence upon the behavior of different ions as they travel through the field. Identification is based on this known field-dependent behavior of different species of ions. Identification of the species may occur by comparison of results observed under one set of field conditions with results observed under another set of field conditions.

Various techniques may also be applied to increase the amount of, or confidence in, the detection data and subsequent identifications. The result is more accurate species detection with reduced false positives.

Figure 1A:
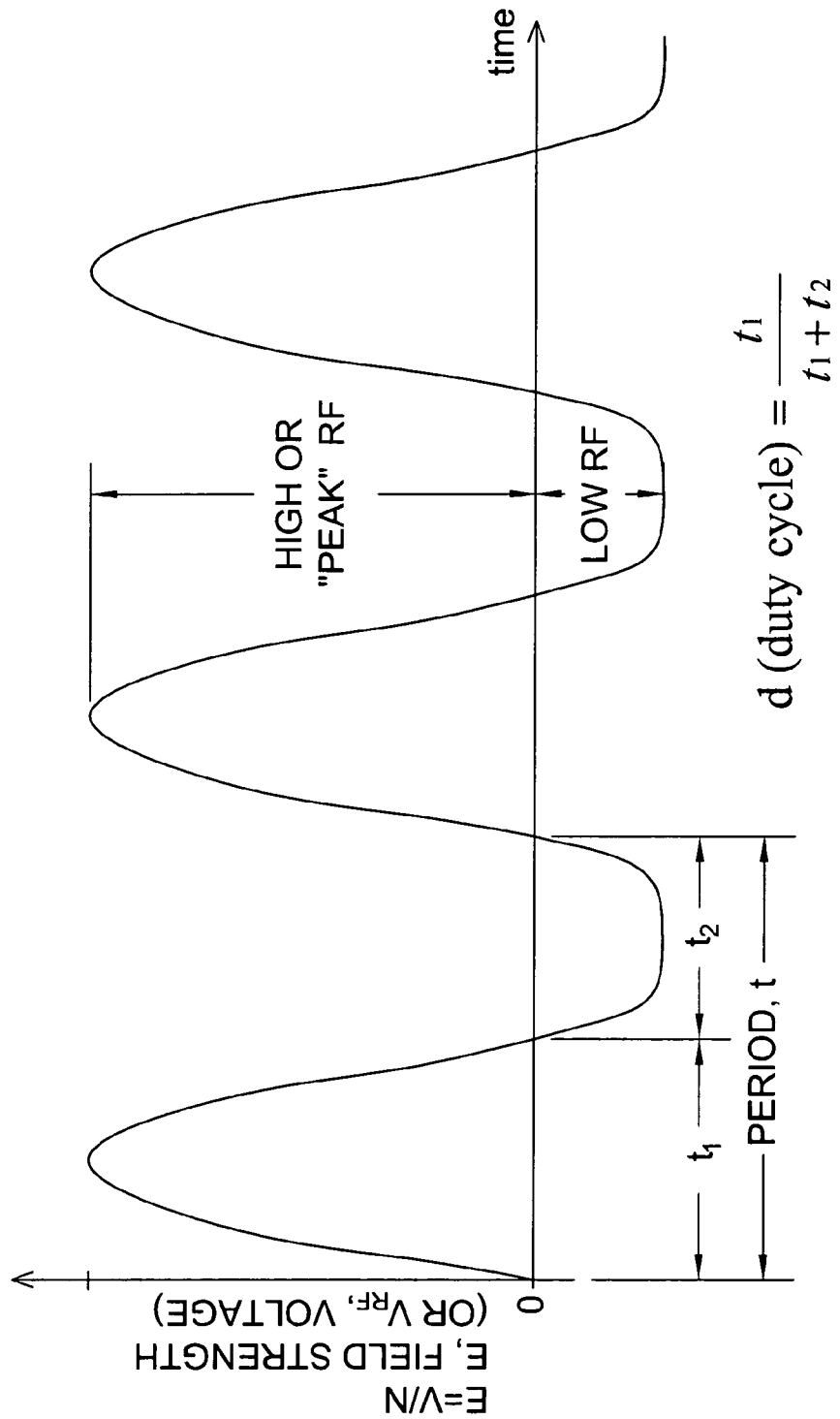
FIG. 1A illustrates an asymmetric field having a peak RF, time period, and duty cycle.
Figures 1, 1B:
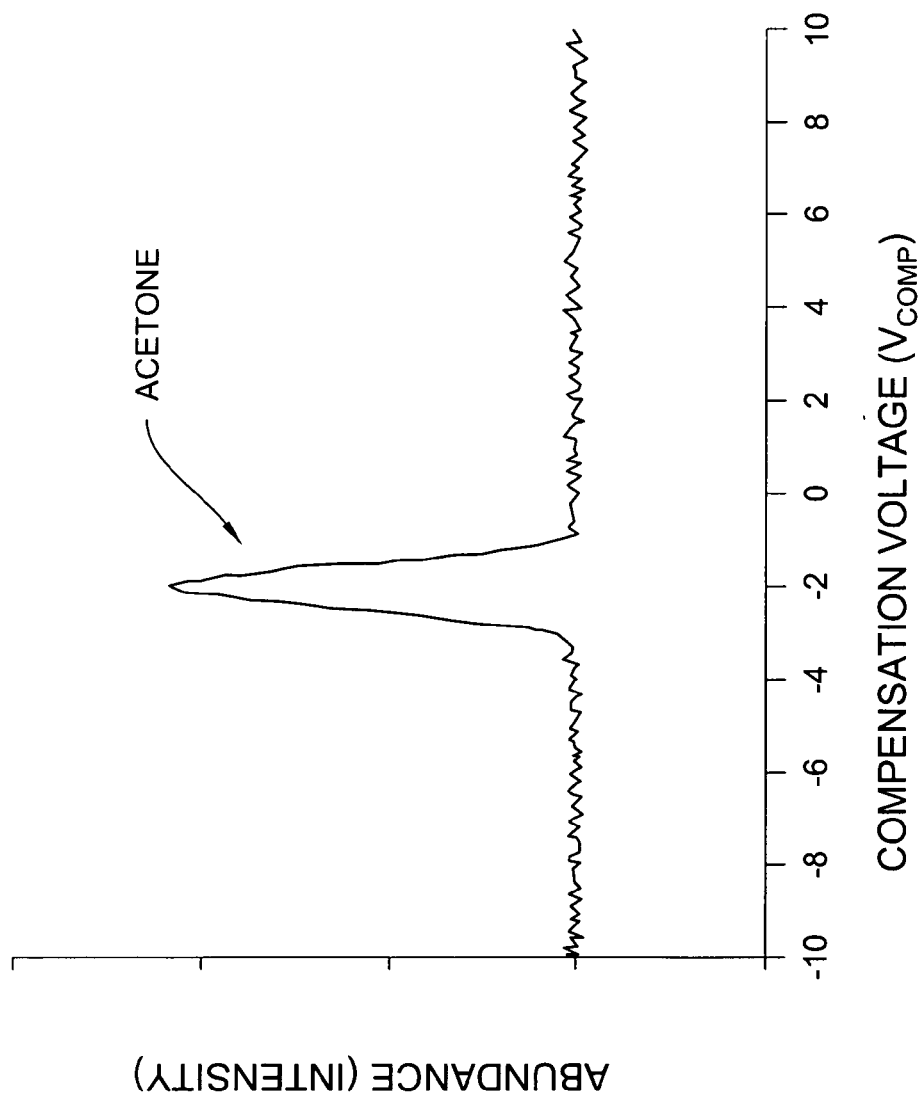
FIGS. 1B-1 and 1B-2 are a typical display of detected abundance versus applied compensation voltage for a given field strength in a field asymmetric ion mobility spectrometer, first for acetone alone and second for a combination of o-xylene and acetone (Prior Art).
Figures 1, 1B, 2:
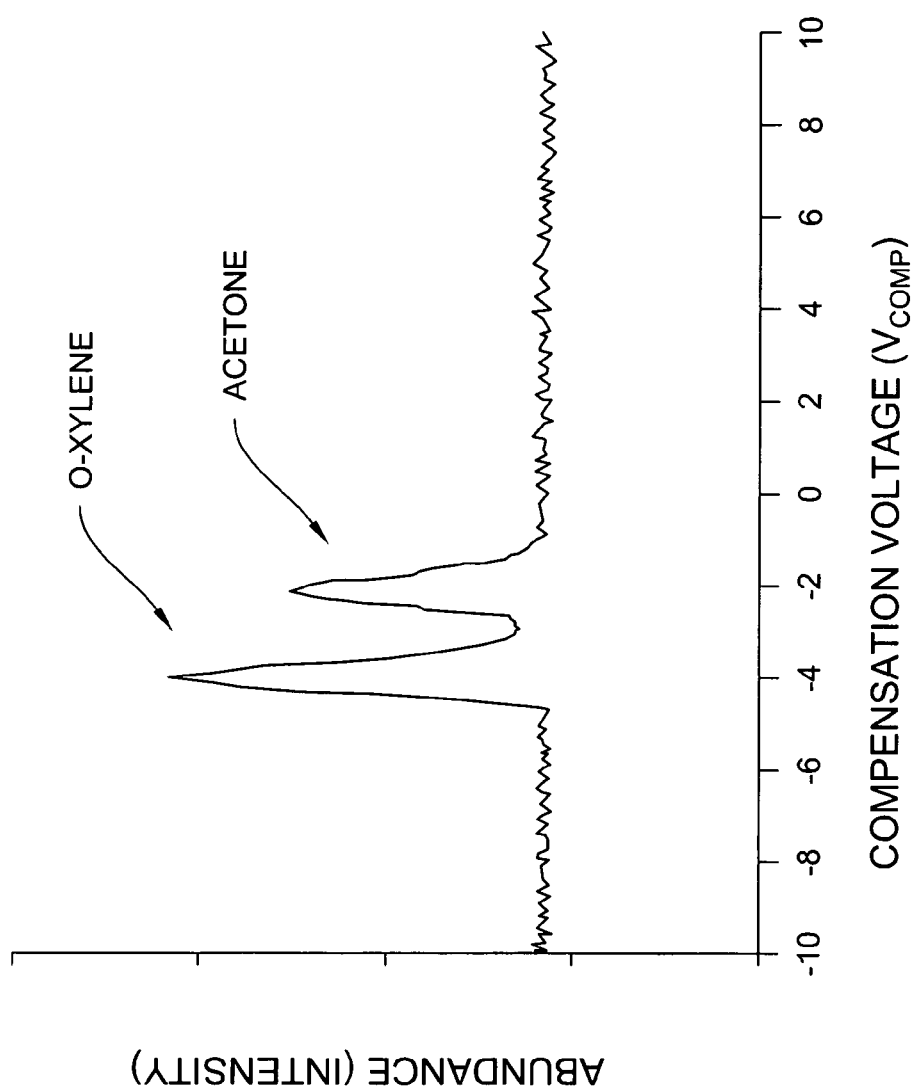

Now more particularly, one device that may make use of the invention, shown in FIG. 2, is a field asymmetric ion mobility spectrometer (FAIMS also referred to as a DMS) apparatus 10. The apparatus accommodates the flow of a carrier gas G which carries sample S from sample inlet 12 at one end of the flow channel 11 to a sample outlet 13 at the other end of the flow channel.

In operation, the sample is drawn from the environment or received from a front end device, such as a gas chromatograph, and flows into an ionization region 14. Compounds in the sample are ionized by an ionization source 16 as the sample flows through the ionization region 14, creating a set of ionized molecules 17+, 17−, with some neutral molecules 17n, of various chemical species that are in the sample S. This may include monomer ions and cluster ions. Such clusters may be created when a monomer combines with water molecules or other background molecules, and the combination is ionized.

The carrier gas carries the ionized sample into the ion filter region 18 in between filter electrodes 20, 22 of ion filter 24. Filtering proceeds now based on differences in ion mobility in the filter field, which is influenced by ion size, shape, mass and charge.

More specifically, an asymmetric field applied across the filter electrodes alternates between high and low field strength conditions in filter region 18. The ions move in response to the field, based on their mobility characteristics. Typically the mobility in the high field condition differs from that of the low field condition. This mobility difference produces a net transverse displacement of the ions as they travel longitudinally through the filter 24, defining an ion trajectory.

In one example, the carrier gas (or other flow mechanism) carries the ionized sample into the ion filter region between the filter electrodes. Filtering proceeds based upon differences in ion mobility, which is influenced by the ion size, shape, mass, and charge. This enables discrimination of ions species based upon their mobility characteristics.

In accordance with the preferred embodiment of the present invention, an asymmetric field voltage or dispersion voltage, variously referred to herein as "RF", "Vrf", or "Vdisp", is applied across the filter electrodes as an RF voltage driven between high and low field strength conditions. This excursion causes the ions to move transverse to the flow as they flow through the flow channel, with the transverse motion being representative of their characteristic ion mobility. Typically, the mobility in the high field condition differs from that of the low field condition. This mobility difference produces a net transverse displacement of the ions as they travel longitudinally through the filter between the electrodes.

The compensation voltage, Vcomp, causes a particular ion species to be returned toward the center of the flow path, thus being able to exit the filter without colliding with the filter electrodes and without being neutralized. Other species will not be sufficiently compensated and will collide with the filter electrodes 20, 22 and will be neutralized. The neutralized ions are purged by the carrier gas, or by heating the flow path 11, for example.

B. FAIMS Device Detecting Response Under Several Field Conditions

Therefore, in the presence of set asymmetric field conditions, as applied through Vrf and Vcomp, discrimination of ions from each other according to mobility differences can be achieved. However, in a single mobility scan, when two ions are compensated by the same compensation signal in a given RF field, there is, in general, no way to discriminate between them after they pass through the filer 24. This would happen where they exhibit the same mobility characteristics for those given field conditions.

In practice of an embodiment of the present invention, however, these ions can be discriminated if they have different polarities, as such is the example with ions 17− and 17+. Thus the device of FIG. 2 can be operated to simultaneously detect both positive and negative ions in the gas flow, enabling identification of two compounds simultaneously or enabling detection of two modes of a single compound simultaneously.

More specifically, the two species of ions 17+ and 17−, enter the detection region 25 where further separation occurs followed by their intensity determination. In a preferred embodiment, the detector 26 includes a first detector electrode 28 and a second detector electrode 30. Electrode 28 may be positively biased and therefore attracts ion 17− and repels ion 17+. Electrode 30 may be biased negatively, and attracts ions 17+ while repelling ions 17−. Thus, this final stage of separation results in the separated ions depositing their charges on the appropriately biased detector electrodes 28 or 30. The signals generated by the ions collecting at detector electrodes 28 and 30 are amplified by respective amplifiers 36 and 38 to provide signals to command and control unit 34.

In the preferred embodiment, the invention applies to high field asymmetric waveform ion mobility spectrometry in a device configuration such that the flow channel 18, filter electrodes 24, and detector electrodes 28 are all provided, preferably in a compact package. This provides for the ability to produce a compact, low cost device which may have incorporated upon a common substrate the various system components and possibly support electronics. Spectrometers according to the present invention may therefore be manufactured using well known microchip manufacturing techniques while at the same time providing highly effective analytical equipment for use both in the field and in laboratory environments.

It is a feature of a FAIMS spectrometer that by application of compensation to the filter field, ions having specific mobility characteristics will be returned toward the center of the flow path and will pass through the filter. Therefore, in practice of the invention, discrimination of ions from each other according to the compensation results in a ions having a particular mobility passing to detector 26 (which may be an on-board electrode arrangement or may include an off-board detector such as a mass spectrometer, for example).

All other species will not be sufficiently compensated and will collide with the filter electrodes and will be neutralized.

In the preferred embodiment, the invention applies to high field asymmetric waveform ion mobility spectrometry in a device configuration such that the flow channel 18, filter electrodes 24, and detector electrodes 28 are all provided in a compact package. This provides for the ability to produce a compact, low cost device which may have incorporated upon a common substrate the various system components and possibly control electronics 40. Spectrometers according to the present invention may therefore be manufactured using well known microchip manufacturing techniques while at the same time providing a highly effective analytical equipment for use both in the field and in laboratory environments.

The control unit 40 contains a number of electronic devices that perform a number of important functions in accordance with the present invention.

These include RF voltage generator 42, compensation voltage generator 44, a microprocessor unit (MPU) 46, memory 47, an analog-to-digital converter 48, and display 49. The microprocessor 46 provides digital control signals to the RF (AKA "dispersion") voltage generator 42 and compensation voltage generator 44 to generate the desired drive voltages for the filter 24, respectively. They may include, for example, digital-to-analog converters that are not shown in detail.

The microprocessor 46 also coordinates the application of specific dispersion voltages Vrf and compensation voltages Vcomp with observed responses from the detector 26, as read through the analog-to-digital converters 48. By comparing an observed response of, for example, peak observed abundance of a particular ion across a range of compensation voltages, Vcomp, the microprocessor 46 can identify particular compounds such as by comparing particular response curves against a library of response curves or other data stored in its memory 47. The results of the comparison operation can then be provided in a form of an appropriate output device such as a display 49, or may be provided by electrical signals through an interface 50 to other computer equipment.

One detailed example of how the microprocessor 46 can detect responses under multiple field conditions is described below in connection with FIGS. 10A–10G.

In practice of an embodiment of the invention, a range of applied peak RF voltages may run from less than 1,000 V/cm to 30,000 V/cm, or higher. The frequency ranges may run from 1 to 20 Megahertz (MHz), with the highest frequencies having an approximately 30 percent duty cycle, although other operating ranges, voltages, field strengths, duty cycles, wavelengths and frequencies are possible in embodiments of the present invention.

In practice of one embodiment of the invention, the processor 46 scans or sweeps a range of compensation voltages (i.e., a scan) for a particular RF field strength as controlled by the applied peak RF (dispersion) voltage for a first measurement set, and then the RF is reset to another level and the compensation voltage is scanned again to establish a second measurement set. This information is correlated with detection signals obtained as set forth above, and compared to look up tables, a compound identification is able to be made.

More generally stated, an object of identification is to detect the intensity of the ions passing though the filter and to associate this intensity with field conditions. Each identified compound is to be associated with at least one particular spectral peak and then we can use the process of peak evaluation or peak matching to identify compounds, peak by peak. This process is not limited to single peaks and multiple peaks detected in a single scan also can be used to define a signature for the responsible particular combination of compounds. If it is a recurring phenomenon, then such complex signature can be part of our table of look up data.

If a particular combination of peaks in a spectral scan is known and important, data representing these multiple peaks can be stored and future detection data can be compared against this stored data. For example, under controls field conditions, such as at raised field strengths, a clustered compound may become declustered. The resulting detection results in a signature of peaks that can be used to identify the source compound being detected even in as detected in a single scan.

In practice of the invention, we have developed an ion mobility-based method and apparatus for detection of sulfur-containing compounds in a hydrocarbon background. In one example, detection and measurement of negative ions is done in a negative mode, and detection and measurement of positive ions is done in a positive mode. The detected data enables a quantitative measurement of concentration of these sulfur-containing compounds, independent of the hydrocarbon background.

C. Positive and Negative Field Measurement

Referring to the illustrative embodiment of FIG. 2, a single positively biased detector electrode 30 (or 28) downstream from the filter can be used to detect the negatively charged ion stream (negative mode), and optionally another other electrode 28 (or 30) may be negatively biased to deflect the negative ions to the positively biased detector electrode. Also, a single negatively biased detector electrode 28 (or 30) downstream from the filter can also detect the positively charged ion stream (positive mode), and optionally the other electrode 30 (or 28) may be positively biased to deflect the positive ions to the negatively biased detector electrode.

Thus, positive and negative modes may be detected in the FAIMS spectrometer, seriatim or in parallel devices. Optionally, in a single scan of a single device, we are able to demonstrate simultaneous collection of multiple data by detecting both modes simultaneously. Referring again to the illustrative embodiment of FIG. 2, in one example, a single positively biased electrode 30 downstream from the filter is used to detect the negatively charged ion stream (negative mode); meanwhile electrode 28 is negatively biased to deflect the negative ions to this positively biased detector electrode 30 so as to improve collection efficiency. However, simultaneously, if desired, the negatively biased electrode 28 detects the positively charged ion stream (positive mode) that is deflected by the positively charged electrode 30.

A detection signal is generated as these ions deposit their charges on a respective detector electrode. These detections can be correlated with the RF signal, compensation voltage and detector bias, to definitively identify the detected ion species. Thus Where two detector electrodes are provided downstream, each oppositely biased, both positive and negatively charged ion species can be detected and identified simultaneously.

In one embodiment, the present invention was used for detection of trace amounts (ppm, ppb, ppt) of mercaptan in varying and even high hydrocarbon backgrounds. The device is also able to characterize hydrocarbon gas backgrounds. For example, the present invention is capable of detecting mercaptans, such as ethyl mercaptan in a methane background, and is also capable of detecting a gas, such as methane, in a mercaptan background.

In this practice of the invention, where mercaptans were detected in hydrocarbon background, the asymmetric voltage applied to the ion filter electrodes ranged from about 900 to about 1.5 kV (high field condition), and a low voltage of about −400 to −500 V (low field condition). The frequency ranged 1–2 MHz and the high frequency had an approximate 30% duty cycle, although other operating ranges are possible. In one embodiment, the detector electrodes were biased at +5v and −5v. Now the mercaptans are detected in the negative mode and the hydrocarbon gases can be detected in the positive mode.

The hardware used to drive the system my be conventional. For example, amplifiers, such as Analog Devices model 459 amplifier, may be used. The signal may be processed in a conventional manner, such as with a National Instruments board (model 6024E) to digitize and store the scans and with software to display the results as spectra, topographic plots or graphs of ion intensity versus time. The ionization source may be a plasma or radioactive source or a UV lamp, or the like.

The present invention recognizes that ions that pass through the filter define a mobility species $17m$. In a further example, this species can be further separated by polarity, such as by correct biasing of the detector electrode pair 28, 30. An example is shown in FIG. 2 where the species defined by ions 17+, 17− passes through filter 24. This species can be further separated to positive and negative species or sub-species by holding one electrode, e.g., detector electrode 28, at one polarity, say negative, and another electrode, e.g., detector electrode 30, at a positive bias. Now ions 17+ will be attracted to electrode 28 and will be detected and ions 17− will be attracted to and will be detected at electrode 30.

Therefore, apparatus of the invention can be operated to simultaneously detect both positive and negative ions in a species flowed from the filter. This enables identification of multiple compounds simultaneously in practice of the innovation.

More specifically, the apparatus 10 discriminates between ions and neutrals based on their mobility behavior, resultant trajectory and polarity. Therefore only ion species 17− and 17+ with a particular mobility behavior and resultant trajectory in the presence of a given compensation bias will be passed by the filter, for a given asymmetric RF field condition.

It will be appreciated by a person skilled in the art that this compensation bias must be established for the compounds being tested. The apparatus of the invention is very stable and test results are repeatable. Therefore, in a preferred practice of the invention, creation of a history table for species of ions detected, correlated with compensation voltage and RF field, enables continuous use of the device without the need for further calibration. However, it is also within the scope of the invention to calibrate the system using the reactant ion peak or a dopant peak, for example.

In one practice of the invention, a mobility species $17m$ was passed by filter 24. That species included hydrogen sulfide ions $17m−$ and methane ions $17m+$, both of which have a similar resultant trajectory, for given compensated asymmetric field. Other positive and negative ions are neutralized given their different and unselected mobility characteristics. (Neutralized ions $17n$ are purged by the carrier gas or by heating the flow path 11, for example.)

The two species of ions $17m+$ and $17m−$ have entered into the detection region 25, where further species separation occurs, followed by detection. In a preferred embodiment, detector electrode 28 is biased positive and therefore attracts hydrogen sulfide species $17m−$ while repelling methane species $17m+$. Electrode 30 is biased negative and attracts methane species $17m+$, while deflecting sulfide ions $17m−$. Thus this final stage of separation results in the separated ions depositing their charges on the appropriately biased detector electrodes (i.e., negative charge on positive electrode and positive charge on negative electrode).

The asymmetric field and compensation bias are generally applied to filter electrodes 20, 22 by drive circuits 32 within command and control unit 34. The signals generated by the ions at the detector electrodes 28, 30 are amplified by amplifiers 36, 38, also under direction and control of unit 34 (communicating by wires, ribbon cable, or the like). A computer (or microprocessor) including a data store, generally shown at 40 correlates historical data for the device with the drive signals applied to the filter electrodes and with detection signals from amplifiers 36, 38, and presents a compound identification information to a readout device 49. In this example, an indication of the amount of hydrogen sulfide and of methane detected would be indicated.

In a particular embodiment, the command and control unit 34 also coordinates ion flow and the application of specific dispersion voltages Vrf and compensation voltages Vcomp with observed responses from the detector 26. By comparing an observed response of, for example, peak observed abundance of a particular ion across a range of peak RF voltages, Vcomp, the microprocessor can identify particular compounds such as by comparing particular response curves against a library of response curves stored in its memory. The results of the comparison operation can then be provided in a form of an appropriate output device such as at a display, or may be provided by electrical signals through an interface to other computer equipment.

In this embodiment of the invention, a single spectrometer device 10 provides a detector with dual detector electrodes 28, 30. One electrode may be positively biased and the other negatively. In the positive mode, the negatively biased detector electrode acts for ions of the same polarity as a deflector electrode, deflecting those ions toward the positively charged detector electrode for detection. In the negative mode, the one detector electrode that is positively biased acts for ions of the same polarity as a deflector electrode, deflecting those ions toward the negatively charged detector electrode for detection. In simultaneous operation, each of these detector electrodes has a dual role, acting as both a deflector electrode and detector electrode, for respectively charged ions.

In practice of one embodiment of the invention, by sweeping the compensation bias over a predetermined voltage range, a complete spectrum for sample S can be achieved. By intelligent control of the system command and control unit 40 it is possible to select specific field conditions and as a result it is possible to allow ion species of interest to pass through the filter while all other candidates are neutralized. In another embodiment, the compensation bias is in the form of varying the duty cycle of the asymmetric field, without the need for compensating bias voltage. In any such manner, the apparatus is tunable, i.e., it can be tuned to pass only desired selected mobility species, which can be further clarified with the above polarity mode detections.

In a preferred embodiment of the invention, the high voltage RF signal is applied to one filter electrode, e.g., electrode 20, and the other electrode, e.g., electrode 22, is tied to ground. A compensation voltage is then applied to one or across the filter electrodes according to the ions species to be passed. It has been further found that biasing the detector electrodes 28, 30, with a floating bias, such as with electrode 28 being held at −5 volts and electrode 30 being held at +5 volts, leads to good performance for detection of mercaptans in hydrocarbon or air backgrounds.

Figure 3A:
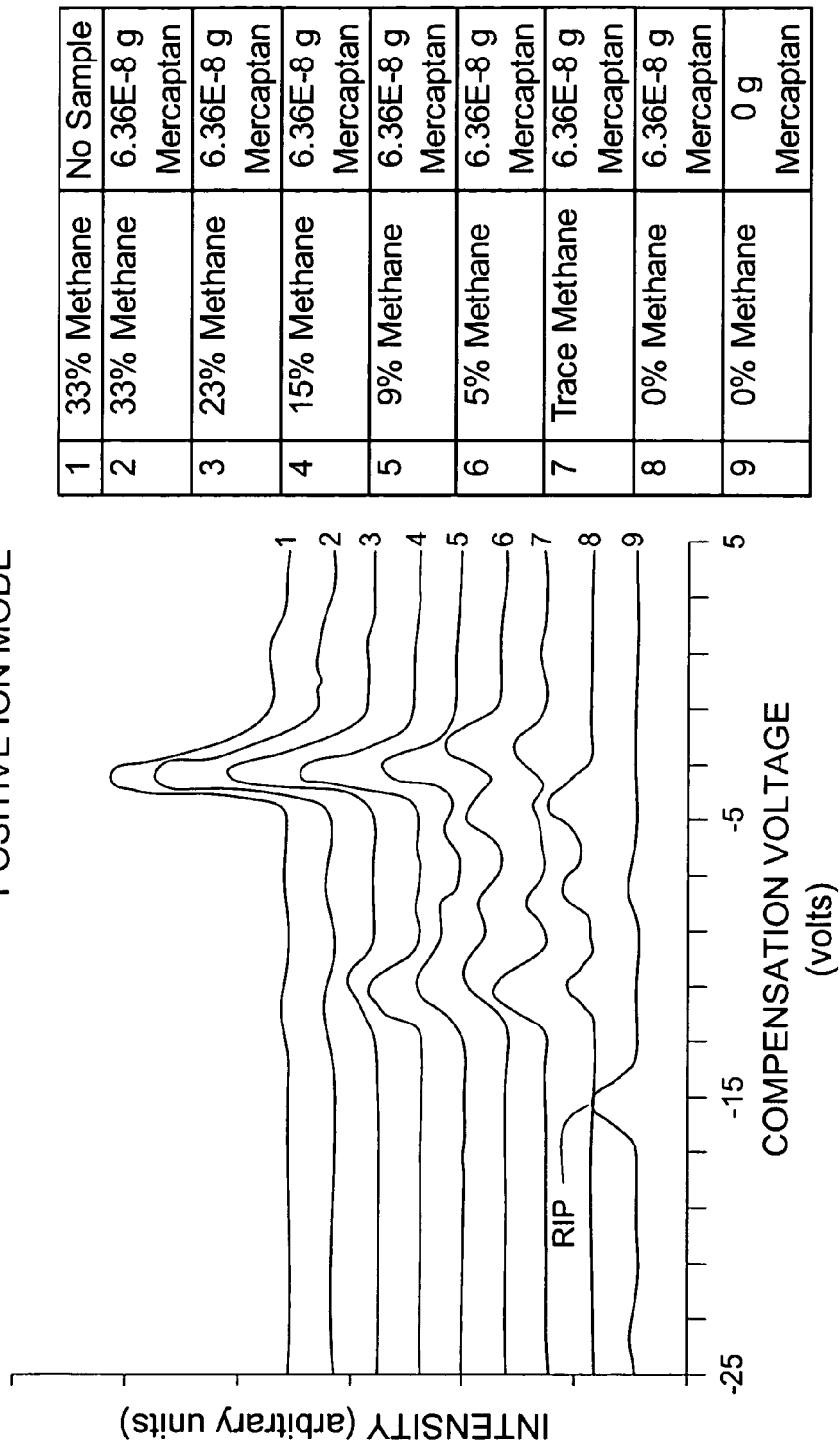
FIGS. 3A and 3B illustrate positive and negative mode spectra for different amounts of ethyl mercaptan in practice of the present invention.
Figure 3B:
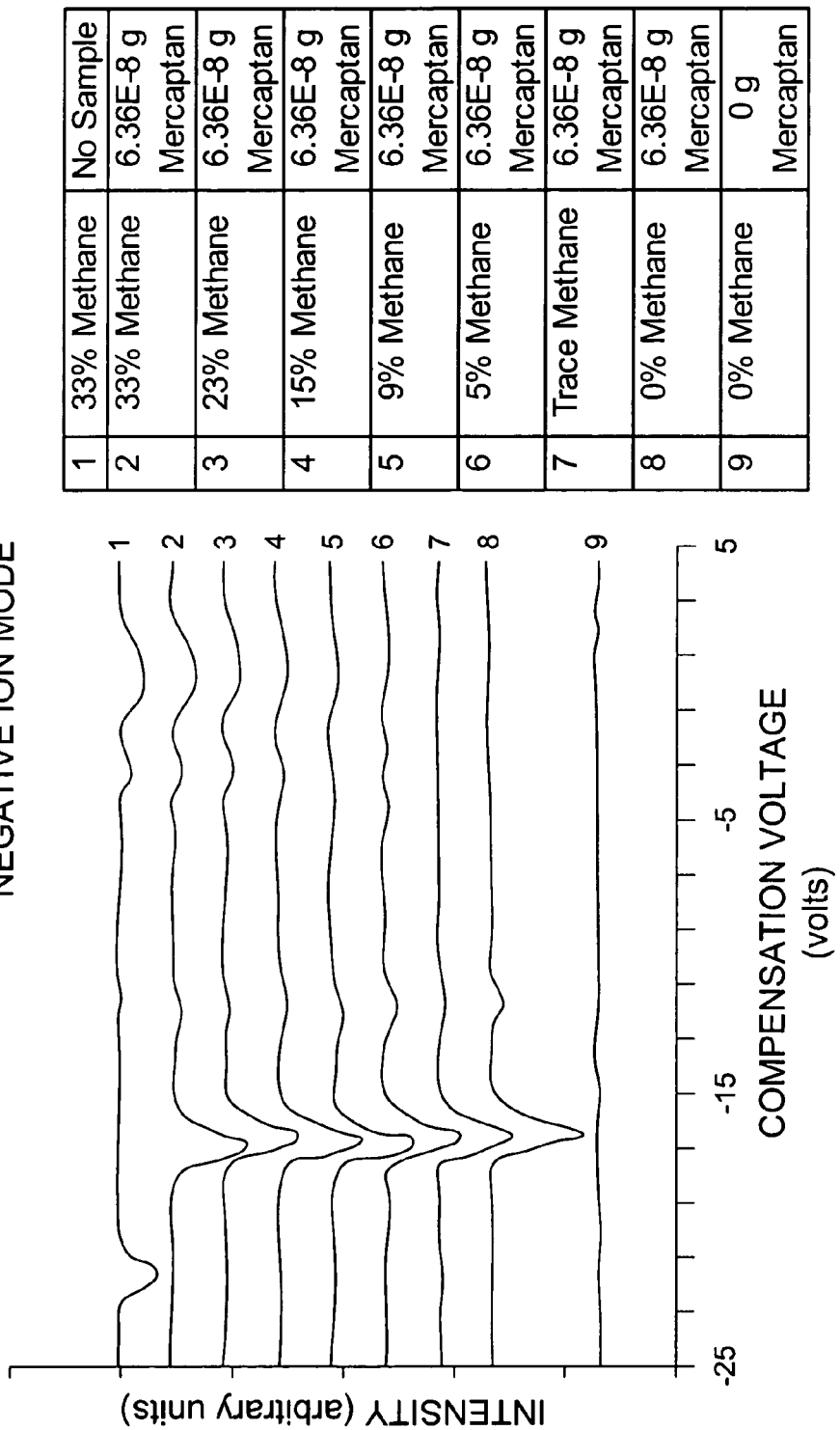

Experimental data verifies viability of this approach. Turning now to FIGS. 3A and 3B, we show detection of ethyl mercaptan independent of varying background gas level. FIG. 3A shows positive ion detection mode ("positive mode") detection, where a detector electrode is negatively biased and attracts positive methane ions 17*m*+ for detection. FIG. 3B shows the effect of varying methane concentration on ethyl mercaptan spectra in the negative ion mode ("negative mode"). Here a detector electrode is positively biased and attracts the negative mercaptan ions 17*m*− for detection.

These spectra are for different amounts of ethyl mercaptan in an air and methane drift gas mixture in positive mode operation and then in negative mode operation of an embodiment of the invention. The mercaptan signatures are clearly captured independent of the air-hydrocarbon drift gas background, at various dosage levels. The detected sample peaks are fully isolated from the background. In FIG. 3A the reactant ion peak (RIP) is clearly isolated; and in FIG. 3B the background is flat.

The foregoing is an example of ionization of a particular compound(s) that results in a combination of positive and negative ions. Both ion types can be evaluated simultaneously in practice of an embodiment of the invention for unambiguous identification of the test chemical. For example, a mercaptan sample when ionized may have predominantly negative ions, but may also include positive ions. Now identification can be more accurate and false positives reduced by using both modes simultaneously to state a unique detection signature. Specifically, while the negative mode fairly identifies the mercaptan, the added positive ion identifier related to mercaptan enables identification in a complex sample. The stored lookup data of known device performance and known species signatures may be accessed for either single mode or simultaneous mode detections. By comparison with historical detection data for the device, these peaks can be clearly identified as the tell-tale spectra of the mercaptan. Both spectra give clear indication of the mercaptan, qualitatively and quantitatively. Running both modes simultaneously clearly identifies the sample with unique and definitive detection data which can be compared to and matched with stored data to identify the detected ions.

Thus it will be appreciated that the present invention is capable of real-time analysis of a complex sample, such as one containing mercaptans and hydrocarbon gas, because these ions are relatively of the same mobility and can pass through the filter under the same field conditions.

Simultaneous positive and negative mode detection in a single mobility scan thus provides a richness of detection data. This increased identification data results in a higher level of confidence, and reduced false positives, in compound identification. This is a valuable improvement over the simple prior art FAIMS method of peak identification.

The data that can be obtained from a negative mode scan is normally different from that of a positive mode scan. While identification of a compound may be achieved by using one mode only, the used of detections from both modes makes for a more definitive identification with lower likelihood of error.

D. Improved Processing of Detection Data

The foregoing demonstrates favorably obtaining multiple detection data from a single mobility scan for positive identification of detected ion species in a sample. This innovation is useful in many applications. Notwithstanding this valuable innovation, we also can obtain a still higher level of confidence, and further reduced false positives, by (1) obtaining multiple detection data from multiple mobility scans, and (2) further processing such data to extract device independent attributes, such as a mobility coefficient, $\alpha$.

1. Multiple Detection Data from Multiple Mobility Scans.

In this "multiple scan" embodiment, ions are identified based on not a single set of field conditions, but based on multiple intensity data detected at at least two and possibly additional numbers of high field conditions (i.e., at at least two field measurement points). Detections are correlated with the applied RF voltage and compensation, at the at least two different field conditions, to characterize a given detected compound. Because multiple detection data are associated with a given ion species of interest, more accurate detections can be made. Comparison with stored data results in reliable identification of detected compounds.

Strategies for identification of detected ions based on data in spectral peaks or in mobility curves include: curve matching, peak fitting, and deconvolution (for overlapping peaks), and like techniques. These techniques enable identification of detected ion species based peaks in a single scan, including simultaneous positive and negative mode detections, and also in multiple scans. The goal is the same: identification of multiple detection data that can be used to definitively identify the species of a detected ion.

More particularly, we have observed that different ion species of chemicals exhibit different mobility as a function of the compensated applied RF peak voltage that generates the high field conditions. Thus, by applying a set of different RF peak voltages and measuring the compensation voltages at the peak locations for the various compounds, we can develop a family of measurement points characteristic of a compound. This family of points can then be plotted to determine the mobility curve signature for specific species as a function of RF peak voltage and compensation. We can record such data and use it for comparison and identification when future detections are made of unknown compounds.

Furthermore, we can extract field condition data, e.g., field strength and compensation voltage for two nearby detections of the same ion species. We can then calculate the mobility curve, or at least the sign and slope of the curve between those two data points as a signature of the detected ion species. We can simply store this data as the signature of that compound along with the field conditions that generated such data. In the future, when two nearby or associated peak detections are made for that species, we again know the field conditions and can compute the sign and slope, or other mathematical variables representing of the curve, for comparisons to the stored data for match and identification. This approach is successful with a high degree of reliability; more complete curve matching is possible but is not required.

As will be appreciated by a person skilled in the art, the selection of measurement points and the number of measurement points may be adjusted for the specificity required for a particular application. The minimum number of measurement points is two, which at least identifies an aspect (such as slope) of the characteristic curve for a compound, given the known field values.

Figure 1C:
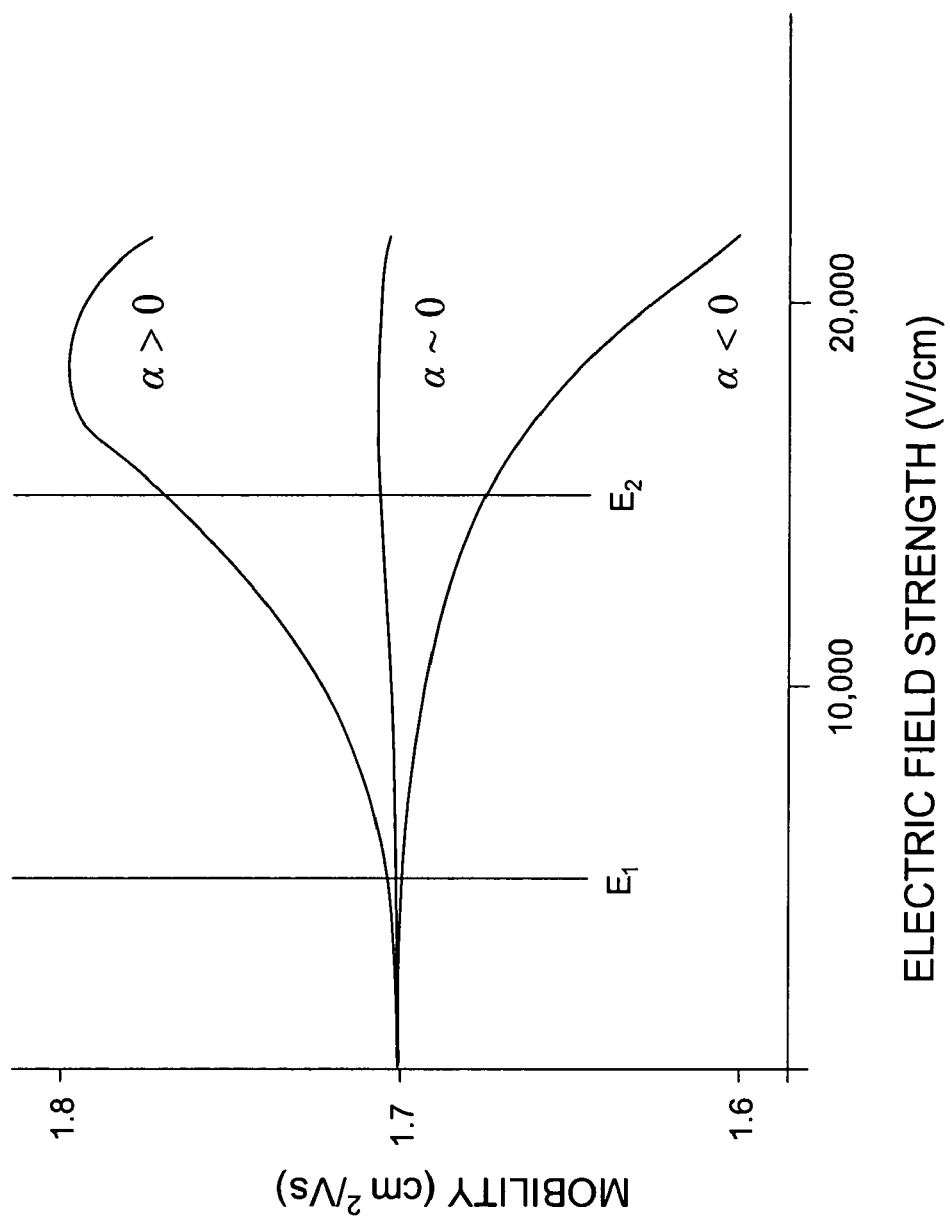
FIG. 1C is a plot of mobility dependence upon electric field strength for three different compounds (Prior Art).
Figure 1D:
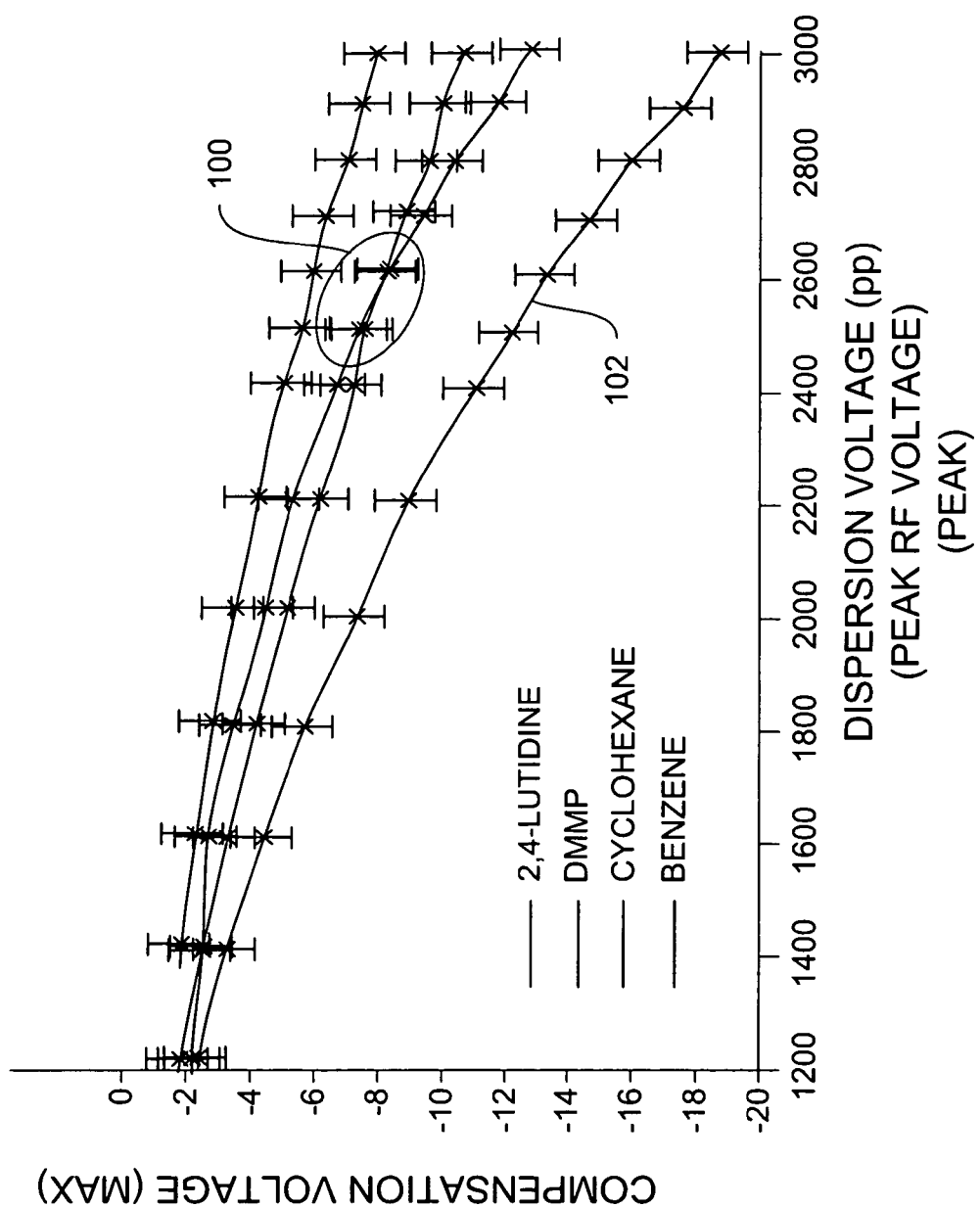
FIG. 1D is a plot showing peak detections across a range of combinations of peak Radio Frequency (RF) voltage and compensation voltage for four different compounds (Prior Art).
Figure 2:
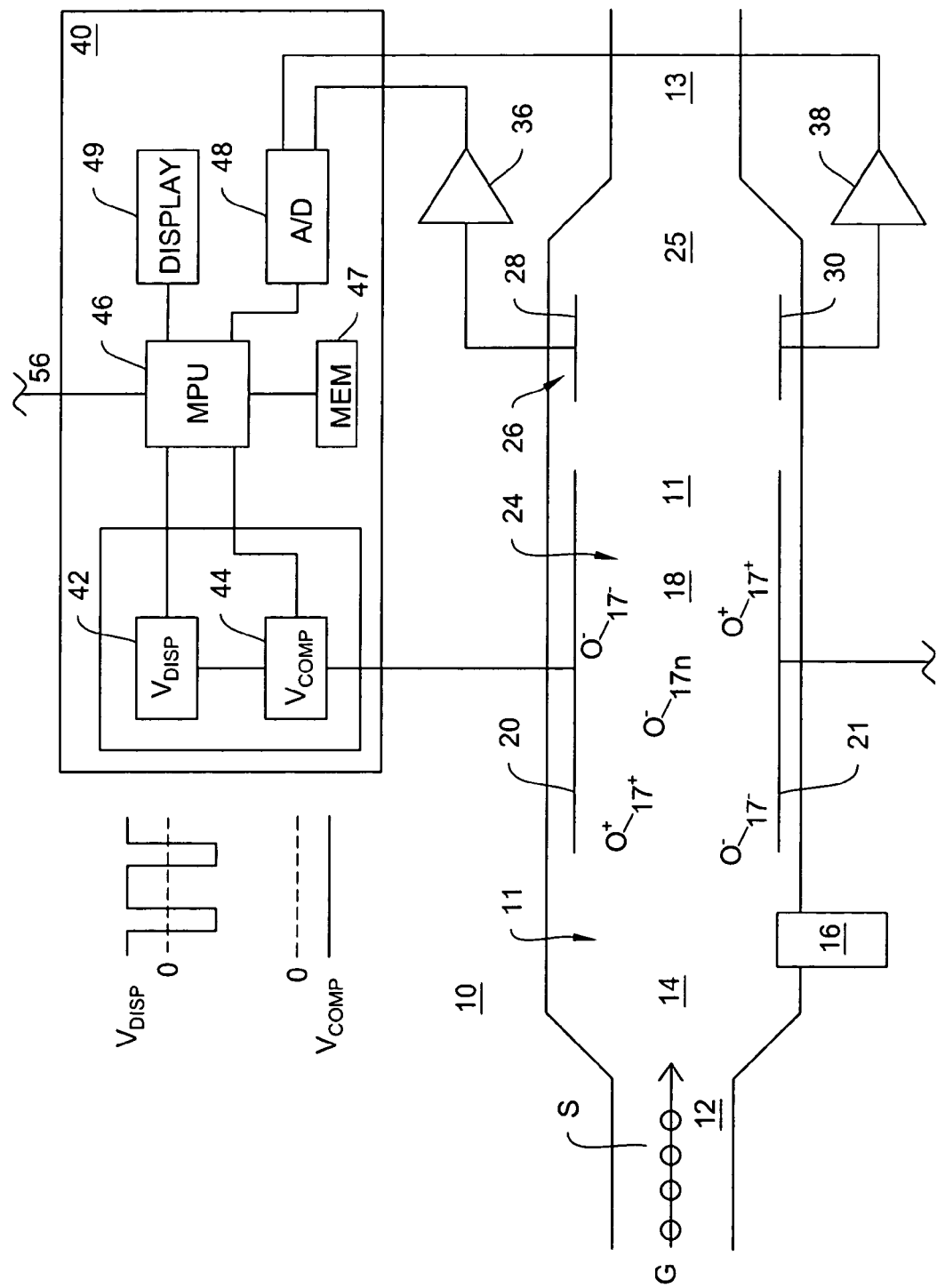

As shown in the multiple scan data collected and recorded in FIG. 1C (prior art), each compound has a unique characteristic mobility curve that expresses the peak detection data associated with that compound at each of various associated peak RF and compensation values. Thus, detection of four different chemical compounds is shown including lutidine, cyclohexane, benzene, and a chemical agent simulant dimethyl-methyl-phosphonate (DMMP). Each curve shows detection peaks at the various field conditions that is characteristic for the compound.

The plot of compensation voltage versus dispersion voltage (i.e., RF peak voltage) in FIG. 1C shows the associated compensation voltage for the spectral peak for each of the particular compounds illustrated at a given RF peak. As is seen from the plot, there is a region (indicated by reference numeral 100) in which the response for DMMP and cyclohexane more or less overlap with one another (i.e., their mobility curves overlap). Therefore, operating in a peak RF voltage region of from approximately 2,500 to 2,650 volts, at around −6 to −8 volts compensation, one would find it impossible to discriminate between the two compounds upon a single scan. In other words, the conventional spectral scan would plot the overlapping peaks as a single peak at that field condition. Peak matching here would be inadequate, except for further software "tweaking" required to separate the peaks. However, this tweaking might not be matched by the stored data of a limited lookup dataset, and therefore identification could fail. This certainly is possible in a portable device that has real world size, space, computing power or other limitations.

We have recognized that by taking a look at an overall response of a FAIMS system to a range of RF peak voltages, over a range of compensation voltages, for a given chemical sample, we can note that each of the curves exhibits a unique signature of field behavior. We call this mobility behavior a signature mobility behavior, and can identify the compounds by this signature behavior.

It will thus be appreciated that a preferred practice of the present invention contemplates stepping the RF peak voltages and scanning the compensation voltages to generate unique sets of data that identify and distinguish the detected compounds to create a data store of mobility signatures. We then have a data to store for lookup that characterizes these mobility curves and can be used for compound identification. This process will be explained in greater detail in connection with FIGS. 10–10F.

We have discovered, therefore, that identification and quantification of unknown chemical species can be improved by generating, for each species, an experimentally determined curve of mobility versus applied electric fields. However, rather than comparing simply the peak observed mobility versus electrical field, mobility is determined over a range of compensated fields, possibly including relatively low voltage field strengths (where mobility may be the same for some compounds) and including relatively high electric field strengths (where mobility is generally different for many chemical compounds). Comparison of a spectral curve or mobility curve generated with the detected data may be made against stored curve data for positive identification.

Thus, by looking at a trend, i.e., the shift of the spectral peak and associated compensation voltages from the first to second field conditions, we can better confirm the identity of the compounds. In other words, other chemical compounds would not have the same combinations of shifts at the same data locations, so that accurate identification is made more likely.

For a generalized example, refer to FIGS. 4A and 4B, showing detection intensity (abundance) as a function of compensation voltage at a particular applied field strength. Note in FIG. 4A that peaks 110-1, 110-2, 110-3, and 110-4 occur at a given Vcomp, with Vrf at 1400v (with a field strength of 28,000v/cm). Accordingly, as Vrf is changed to 1450v (field strength of 29,000 v/cm), shown in FIG. 4B, the set of peaks shifts to location at different Vcomp. Thus it is clear that applying even a slightly different field condition will result in peak locations being at least slightly displaced, as indicated by shifts in associated compensation level. These observations can thus be used in a process of identifying detected ion species by collecting RF and Vcomp levels and correlating with detection data and then performing a comparison with stored identification data for known ions species. Upon making a match or near match, an identification of the detected species can be made.

It will now be understood that it is possible to control field conditions and to discriminate between compounds that are ordinarily difficult if not impossible to separately identify by other means. Selection of field conditions enables isolation of an ion species of interest. Furthermore, because the system of the invention matches detection data with stored data, we can select field conditions that will produce detection data that is matchable to stored data, assuming the relevant ion species is present in the sample.

Turning to FIGS. 5A and 5B, we demonstrate the selectivity available in practice of the present invention. In FIG. 5A, in a field strength of 24000 v/cm, peaks for three different isomers of xylene in a sample, p-, o-, and m-, were detected. In FIG. 5A, the peaks for p- and o- are indistinguishable while the peak for m- is well defined. In order to further evaluate the sample, we perform a second detection, shown in FIG. 5B in a lower field strength of 18000 v/cm, where peaks for the three different isomers of xylene are clearly distinguished and identifiable.

It is therefore an additional recognition of the invention that better discrimination between species is not always a result of higher field conditions, as. In fact, in this example, the p- and o-xylene isomers became distinguishable at reduce field strength. Again, now species identification is by table lookup, preferably of multiple detection data, and regardless of whether based on an increasing or decreasing set of field conditions.

What is important to recognize here is that simply increasing the field strength does not necessarily increase resolution as has been suggested by others (see U.S. Pat. No. 5,420, 424). In fact, to check for the presence of a combination of compounds (or of isomers), or upon collection of detection data that suggests such presence, multiple detection data may be collected and used together to form a signature for the detected ions. Now comparison to stored data may provide identification of a single species or may provide identification of a typical grouping. For example, the detection data represented in FIG. 5A or 5B alone are each characteristic plots of the three xylene isomers; alone these plots enable some identification but together they enable a very high degree of assurance that the three xylene isomers have been detected. Therefore, a match to stored data for both field conditions for these isomers would provide a reliable ion species identification with low likelihood of false positives. Furthermore, a hand-held device that merely looks at these two or similar "data points" would be delivered in practice of the invention as a handy xylene detector.

In another example of the invention, we generate detection data over a range of applied field conditions. For example, in FIGS. 6A and 6B we show the effect of changes in field strength on the location of detection peaks at different compensation levels for hexanone and octanone. These figures present a series of plots of the response of a FAIMS device with different applied field strengths. The curves are offset on the vertical axis, with the offset increasing as electric field strength increases. While various operating ranges are possible, as an illustration, FIGS. 6A and 6B may be understood as presenting the peak RF between a low of around 620 volts (lowermost plot in each) and a high of around 1450 volts (uppermost plot in each). Several attributes are noted in this series of responses. For example, paying attention specifically to the hexanone plot of FIG. 6A, a monomer peak of 601-1 of particular interest is somewhat obscured in the lowest field strength condition. However, at the highest applied field strength, the peak 601-m corresponding to hexanone is clearly discernable from the other peaks.

Several phenomena have occurred with the increase in increasing applied field strength. First, we note that a reactant ion peak (RIP) 605-1 was relatively dominant in the low field voltage reading. However, as electric field strength is increased, the RIP 605-m shifts to the left at a more rapid rate than the monomer ion peak 601-m of interest. This is because the α parameter, of the mobility coefficient for the reactant ion species, is different than the α parameter for the monomer ion of interest.

In addition, we note that the relative amplitude of the reactant ion peaks 605 decreases markedly with the increase in the electric field. Thus, RIP 605-m is observed at much lower amplitude and well separated from the monomer peak 601-m of interest at a specific field condition. While the monomer peaks 601 also shift, they do not shift by the same amount, or even as much. Thus, by analyzing the compound over a range of applied field conditions, a condition can be discovered at which the RIP 605 will shift away from, or perhaps even shift off the scale of, other observed peak voltages. In some cases this allows easier detection of the monomer ion peak 601 of interest.

Similar behavior is observed in the monomer peaks 610-1, 610- . . . , 610-n observed for octanone and the resulting reactant ion peaks 615-1 to 615-m. This information can thus be used to identify a species by comparing a family of response curves to a stored family of known response curves.

Another observed effect in both FIGS. 6A and 6B is that a so-called group of cluster ions 608, 610 are seen. The cluster ions 608 represent clusters of chemical materials in the sample. Typical cluster ions, having a heavier chemical weight, have peaks that are shifted differently from monomer ion peaks of interest. In particular, given that they are heavier, the cluster peaks shift differently. In this example, the cluster peaks shift in a direction away from the direction of shift of the monomer peaks with increasing applied field strength. This characteristic feature of cluster ions observed with this sample can also be stored and utilized in recognizing the hexanone or octonone ions.

These curves shown in FIGS. 6A and 6B are but one example of how applying a range of field conditions to detect a given sample can be utilized to advantage. Another effect can be observed with the application of relatively high field strengths. Specifically, complex ion groupings can be fragmented with higher field strength so that the components of the group themselves can be individually detected.

For example, Sulfur hexafluoride (SF6) can be very well detected in the negative mode. However, the response in the positive mode, while alone not definitive, has a profile and thus in combination with the negative mode is confirmative and provides a lower likelihood of false detections. We therefore can detect SF6 in the single mode of dual mode, seriatim or simultaneously.

SF6 gas is used in atmospheric tracer applications to monitor air flow, as a tracer for leak detection in pipes to point detect sources of leaks, in power plants to isolate switches to reduce, or prevent breakdown of the switches, among other uses. Isolation and detection of SF6 is often found to be a difficult proposition.

In practice of the present invention, it is possible to detect SF6 in air, getting a very distinct peak for the SF6 separate from the reactant ion peak. The reactant ion peak is composed of the ionized nitrogen and water molecules in the air.

Figure 3C:
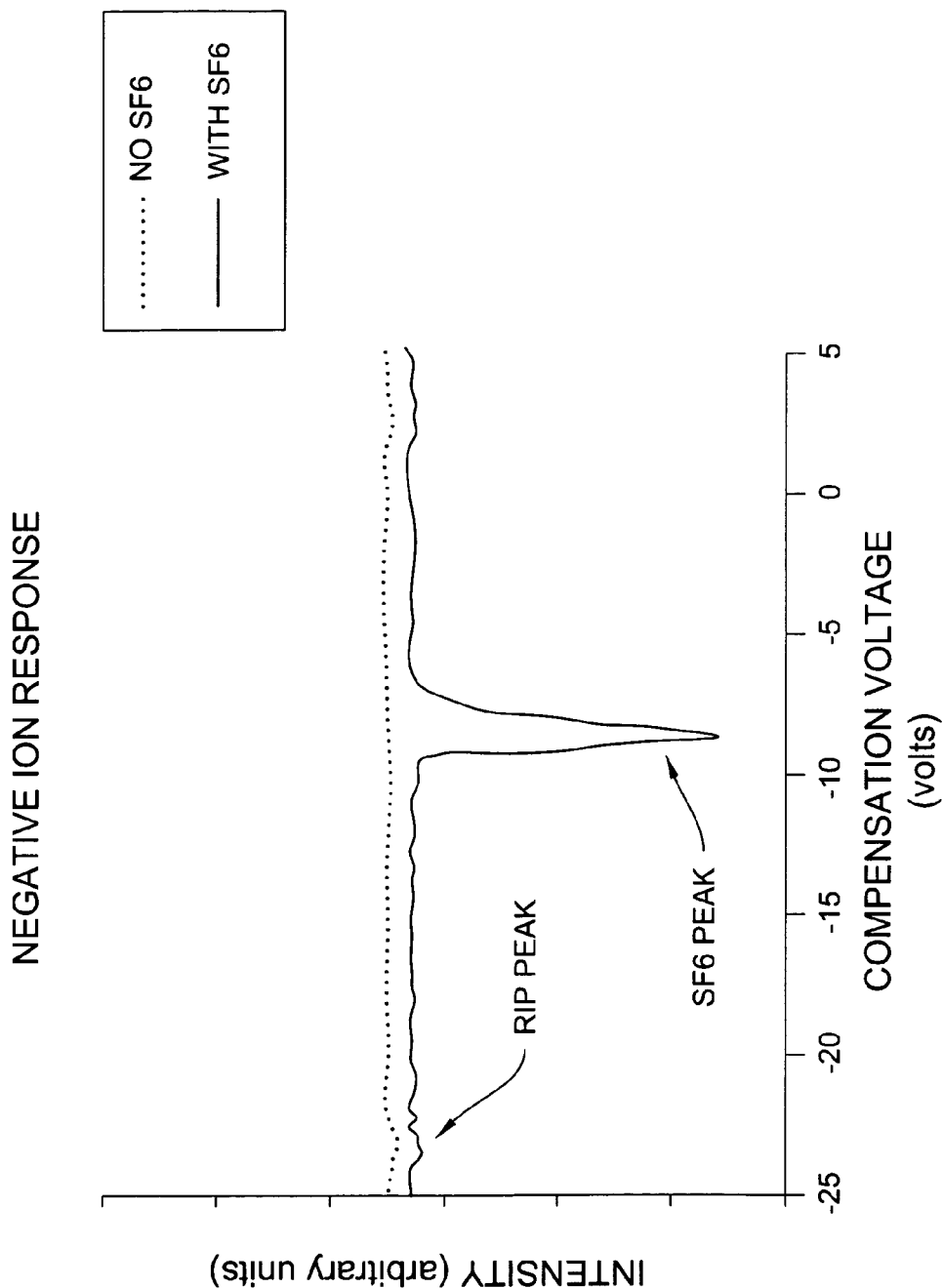
FIGS. 3C through 3G illustrate the affect of changes in field conditions, such as changes in compensation, on specific spectra, and showing divergent behavior of monomer and reactant ion peak (RIP) detections with changes in field for detecting sulfur hexafluoride (SF6) in practice of the invention.
Figure 3D:
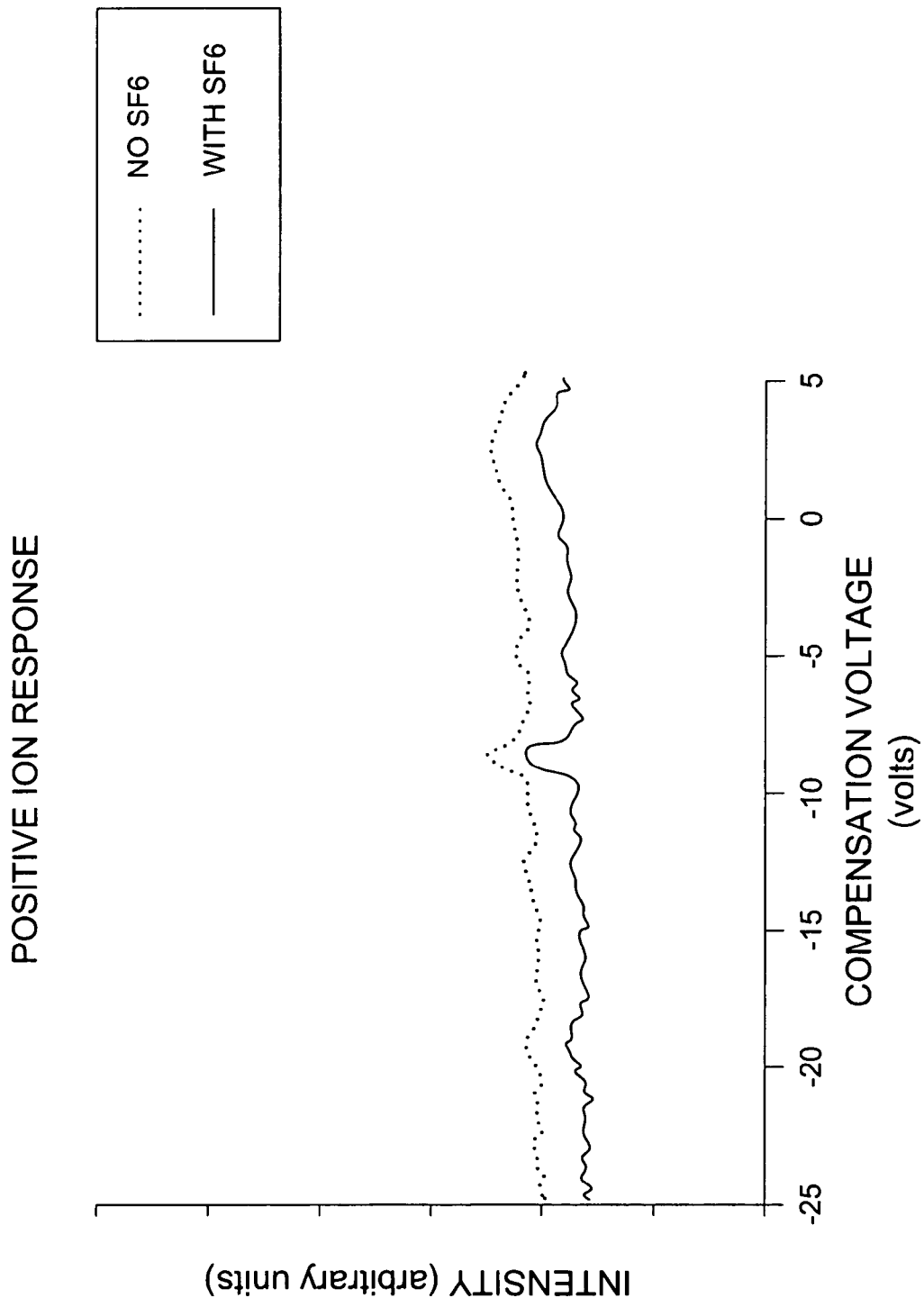

In conventional IMS (time of flight) the reactant ion peak overlaps the SF6 peak. In practice of the present FAIMS innovation, in the negative ion mode (i.e., detecting negative ions passing though the FAIMS filter based on RF and compensation as shown in examples below), it is possible to clearly separate between the SF6 peak and the reactant ion peak (RIP). This success in the negative mode separation between SF6 and the RIP peaks is clearly shown in FIG. 3C. However, in the positive ion mode, there is no detected difference between the signal without the SF6 present and with the SF6, as shown in FIG. 3D.

Figure 3E:
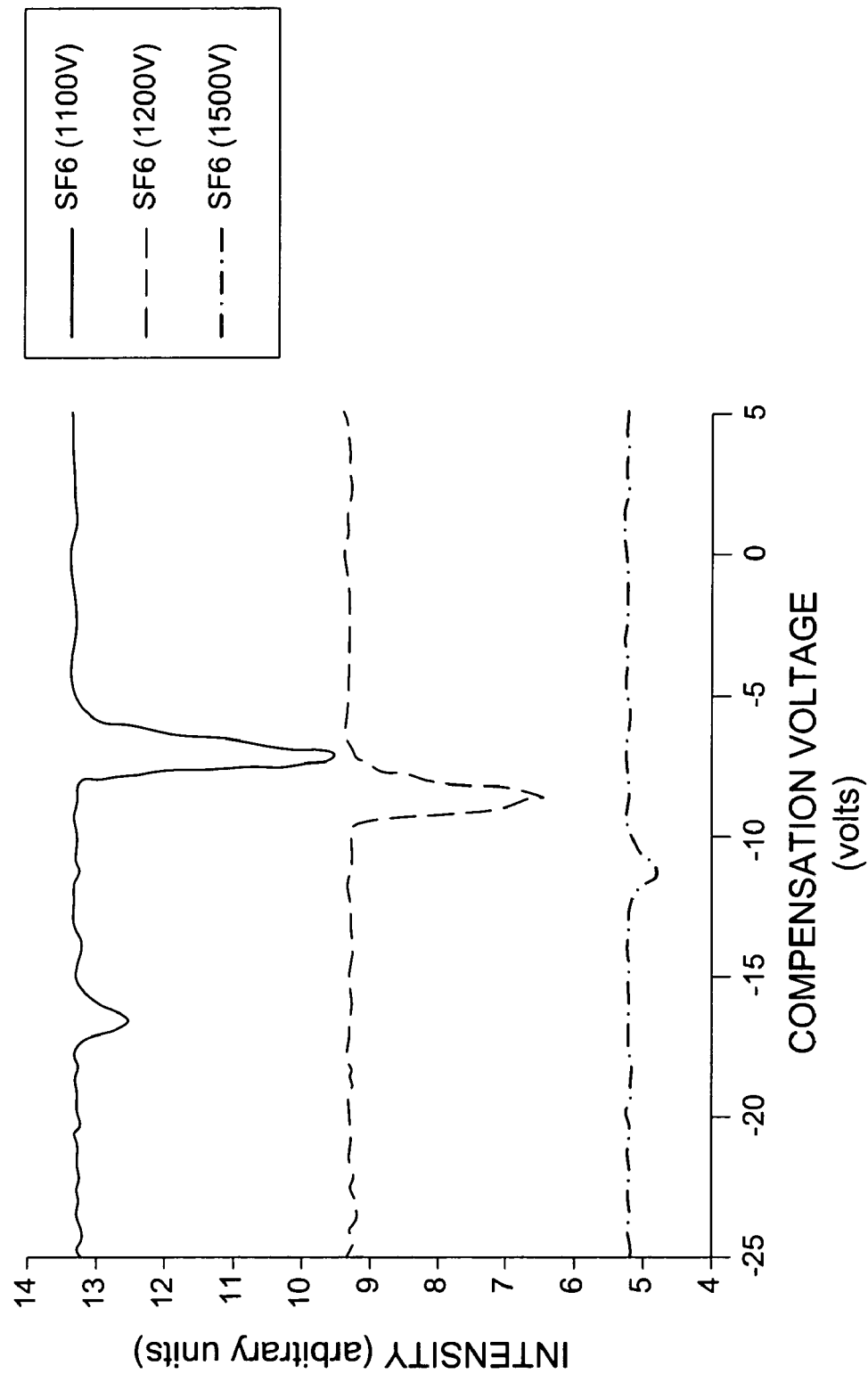
Figure 3F:
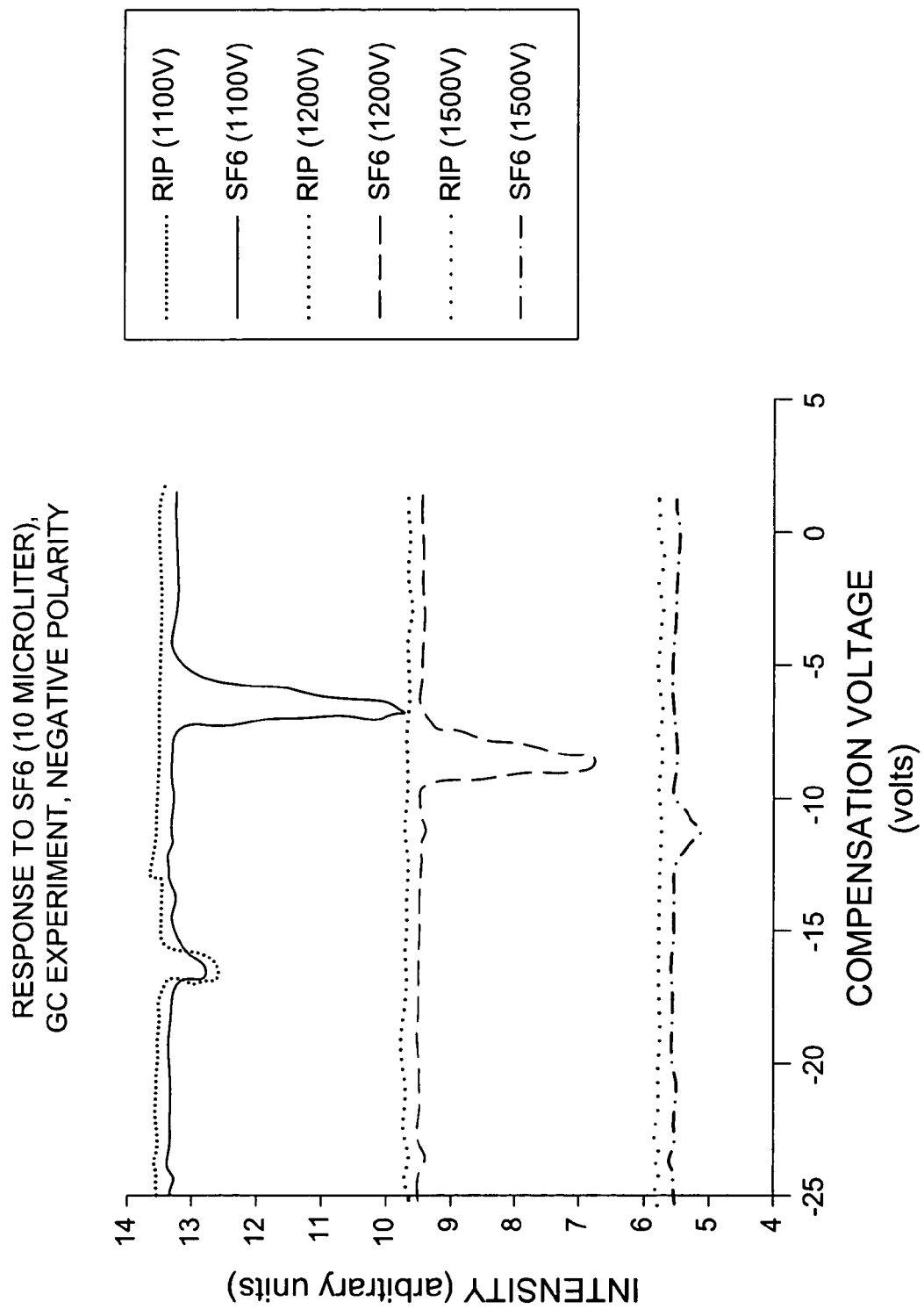

In FIG. 3E, there is a plot of the FAIMS response at different RF voltage levels in the negative ion mode. FIG. 3F shows this result and also shows the RIP detected in absence of SF6. Thus clear vitality of the FAIMS filter of the invention with appropriate selection of RF and compensation voltages is shown. In both cases the SF6 peak is shifted from and distinct from the RIP.

Figure 3G:
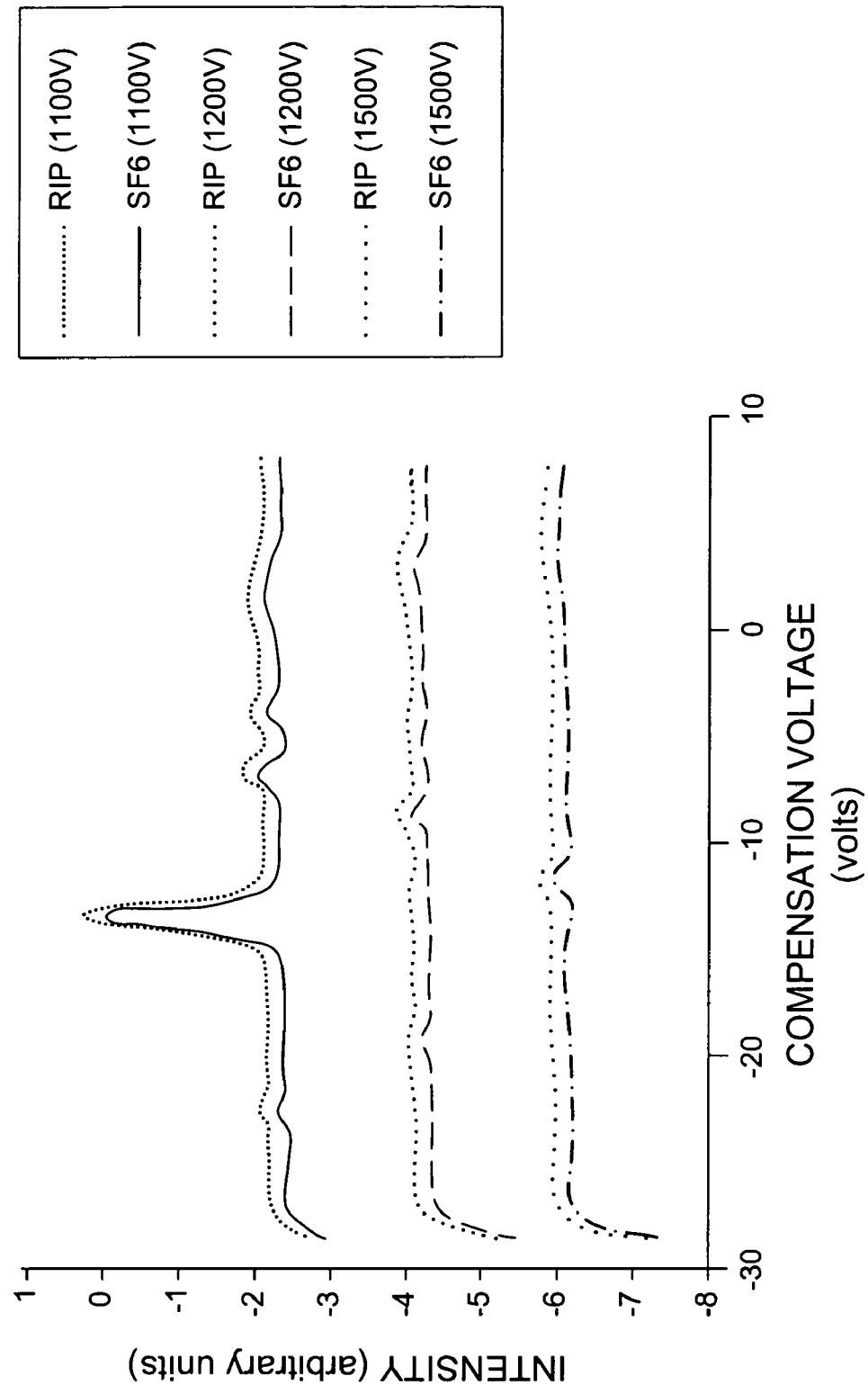

FIG. 3G shows that FAIMS response in the positive ion mode (detecting positive ions passing through the FAIMS ion filter), where the SF6 peak is not isolated from the RIP. While alone this is not definitive, it is an expected detection and therefore may be used as confirmative when combined with a definitive SF6 negative mode detection.

In one embodiment of the invention a portable battery powered unit for the detection of SF6 with a sensitivity of 1×10−9 atm cc/sec SF6 (0.01 PPM) is enabled. In this embodiment, the invention may be used, for example, in the power industry to ensure the leak tightness of High Voltage Switchgear and in the laboratory for testing fume hoods to the ASHREA 110 specification. Other applications include torpedo head, pipework systems, and air bag integrity testing. The high sensitivity, rugged design and ease of use and set up of the invention are advantageous for many applications that involve the detection of SF6.

Figure 7:
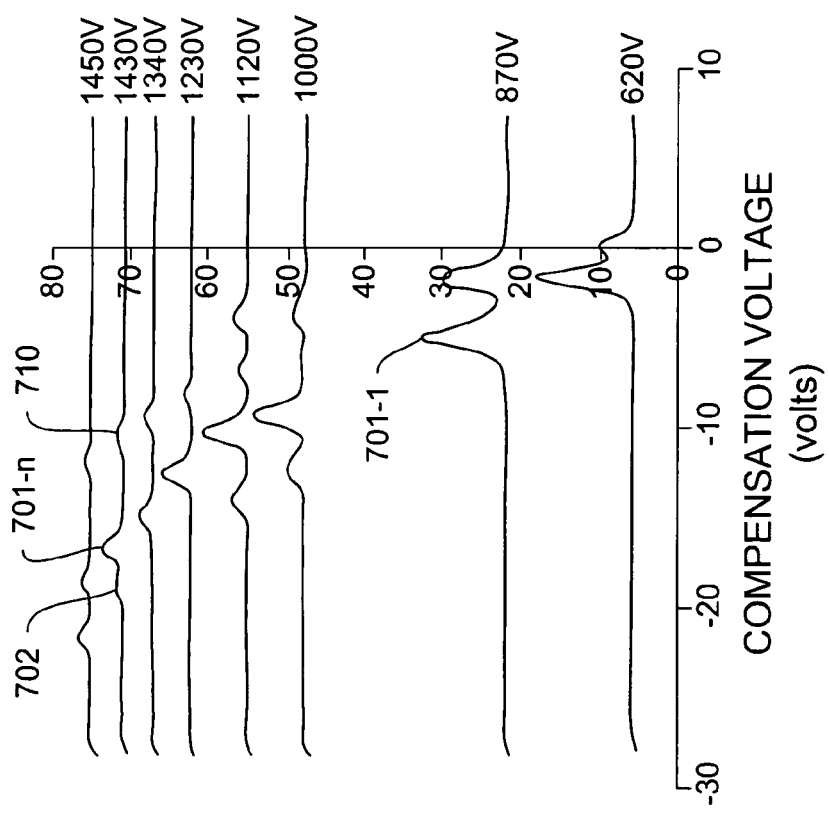
FIG. 7 illustrates effect of changes in field conditions on location of individual detection peaks and ability to separate peaks in practice of the present invention.

FIG. 7 is an example of such an affect on a mercaptan ion sample. In particular, a range of background voltages (from 620–1450 volts) were applied to an ethyl mercaptan spectra in which we see a general shift of ion peak behavior as an electric field conditions are strengthened. However, we also observe a fragmentation condition. Specifically, at lower applied field conditions, strong single peak is observed, such as at 701-1. However, as electric field strength is increased, multiple peaks 701-n, 702, . . . 710 are observed in a spectra. By observing and recording the peak locations not only at the low volt field conditions, but also at a range of field conditions, this fragmentation behavior can be further exploited to better identify compounds. We can store data indicating the peak RF voltage at which fragmentation occurs, or the locations of the fragment peaks, and then further use it when matching detection data.

Figure 8A:
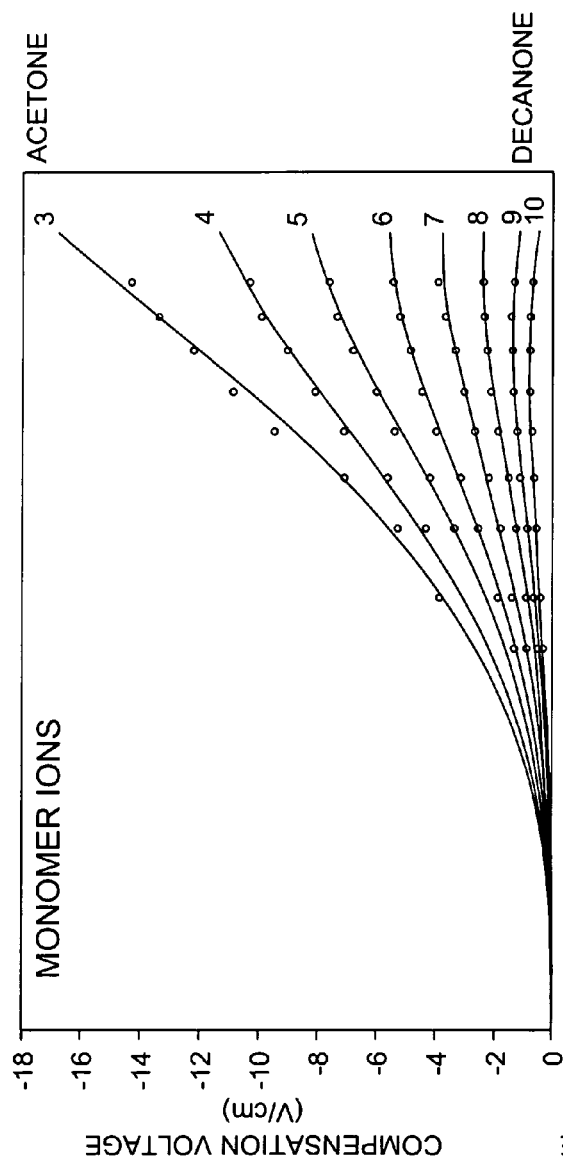
FIGS. 8A and 8B respectively show a plot of compensation versus field strength for detected monomer and cluster ion peaks for a family of ketones in practice of the present invention.
Figure 8B:
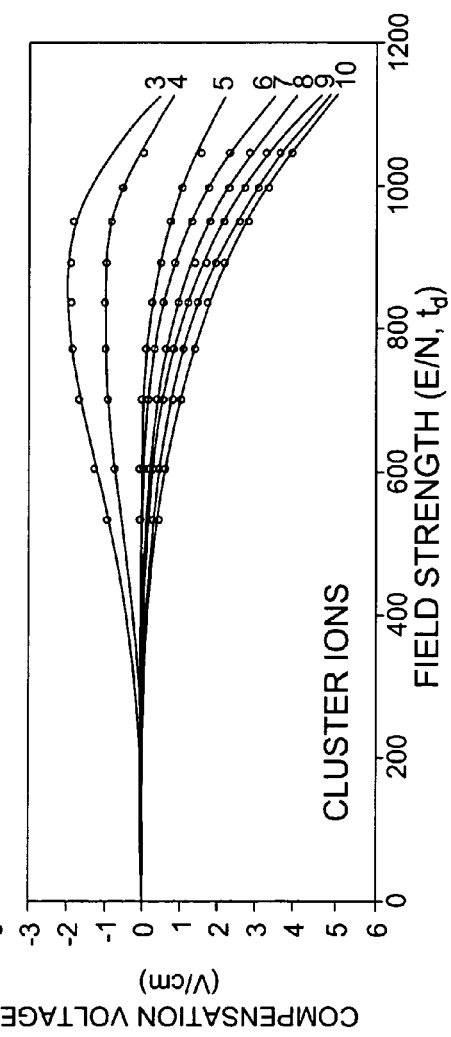

We have also been able to discover species identification method that is device-independent. Turning now to FIGS. 8A and 8B, we have plotted experimental detection data recorded in Table 1 (FIG. 8C) for a homologous group of ketones, including: acetone, butanone, pentanone, hexanone, heptanone, octanone, nonanone, decanone (8A— monomers, 8B—clusters). Each species has a unique mobility curve, and thus a unique mobility signature, for the given set of field conditions. We can store this data and then use the same device as a detector for ketones. We obtain a set of detection data and perform curve matching versus the stored data or other data comparison. A match enables identification of the detected ketone in that device. We also can take any two sets of points and store curve data, such as slope and sign, for the experimentally detected data for a known species. Now with two detections, such as at peak RF field strengths (E) of 28000 and 29000 v/cm, we have two data points, between which we can compute slope and sign for a purported connecting curve function, and then we compare to stored data to make a positive identification of a detected species in that device.

However, we can go a step further by making the identification process device-independent. Thus we create data that can be used in any system that detects field mobility dependence of an ion. This is based on determining the parameters of a function derived from the fundamental mobility coefficient associated with each species.

Therefore, for example, the multiple data represented in FIGS. 4A and 4B and 5A and 5B each can be used to provide positive identification of a detected species by the unique and inherent mobility characteristic that identifies that species. We make this comparison to a lookup table that can be specific to the device in question, but also can be a universal set of data that is device-independent. Thus, in general, one does not wish to only compare the plot of abundance curves versus compensation voltage individually, but rather generate a plot of observed peak locations for specific compensation voltages, so that curves, slopes, signs, and various details can be discerned for each of the detected ions for comparison to a library of lookup data.

2. Alpha Coefficient Determination

More specifically, in computing mobility signatures, we have found that an expression of the field-dependence of ion mobility, the so-called α coefficient, expressed as a function of field, can be used to generate a unique α function that is inherent for that species and is device independent. Thus the α function can be used as the unique signature of a species; quite remarkably, this function expresses both a characteristic signature for the ion species and is device independent. In short, we recognize that peaks change position in signature ways because they have different alpha signatures.

Thus we use the α function as a mobility signature for detected species. The signature can be determined for a detected unknown compound based on the field conditions that are used, and then this can be used to make an identification according to a lookup table of stored known signature data associated with known compounds. More particularly, in practice of a preferred embodiment of the invention, ion species are identified based on the mobility dependence of the species under various field conditions. Data is collected for the sample under test for at least two field conditions, the data is processed, and a comparison of detection data computed as an α function for the sample under test versus the stored data enables identification of the compounds in the sample.

Referring again to the discussion of the α parameter, FIG. 1B is a plot of mobility versus electric field strength for three examples of ions, with field dependent mobility (expressed as the coefficient of high field mobility, α) shown for species at a greater, equal to and less than zero. For any given set of field conditions, the field strength and compensation can be correlated with an α value. This is shown in the work of Buryakov et. al., *A New Method Of Separation Of Multi-Atomic Ions By Mobility At Atmospheric Pressure Using A High-Frequency Amplitude Asymmetric Strong Electric Field, Intl J MassSpec and Ion Proc.* (1993), at p. 145.

We have observed that knowing the a parameter alone at a particular field strength does not prevent false positives. This would occur at the intersection of the two plots in FIG. 1C, at the point indicated by reference numeral 100. Without more information, knowledge of the α parameter for the respective ion species at that location does not provide unique mobility signatures for both compounds. Thus, without doing more, any number of readings at this intersection is likely to result in a detection error.

However, we have also found that we can express an ion's α mobility characteristic as a function of field, i.e., as α(E), and can define a unique mobility signature for the ion species which is device-independent. This α(E) or "alpha function" relates the size, effective cross-section, shape, and mass of the ion to field conditions. It is understood that as the applied electric field increases, the increasing electric field tends to displace, stretch, and/or breaks the bonds of the ion such that the stronger the field, the greater the induced dipole, quadripole, or higher order moments of the ion. These, in turn, affect the relative mobility of the specific ion. The result of relating these aspects is to define a unique mobility signature for the ion species of interest. This also turns out to be device-independent.

The relationship of the α(E) function to field conditions is shown in the following:

$$V_c(E) = \frac{<\alpha E_s f(t)>}{1 + <\alpha> + <\frac{d\alpha}{dE}E_s f(t)>} \quad (1)$$

where: Vc-compensation voltage (peak position); Es-electric field strength; f(t)-waveform parameters (waveshape and so forth).

Thus for each spectral detection, we can compute α as a function of field conditions, i.e., α(E). Specifically, the asymmetric waveform in a field asymmetric waveform mobility spectrometer, $E_{max}(t)=E_{max}f(t)$, is designed to satisfy the following conditions:

$$1/T \int_0^T E_s(t)dt = <E_s f(t)> = 0 \quad (3a)$$

$$<f^{2n+1}(t)> \neq 0 \quad (3b)$$

where $f(t)$—is a normalized function which describes the waveform, and $E_{max}$ is the maximum amplitude of the waveform. The waveform is designed such that its average value is zero (equation 3a) while the polarity of the electric field during one period is both positive and negative. The addition of the compensation field, C, to the waveform $E_s(t)$ yields Equation 4:

$$E(t)=E_s(t)+C=E_s f(t)+C \quad (4)$$

so the average ion velocity over a period of the asymmetric waveform can be written as:

$$V=<V(t)>=<K(E)E(t)> \quad (5)$$

Only ions with average velocity of zero, v=0, will pass through the gap without neutralization. An expression for the compensation field required to enable an ion to pass through the gap can be obtained by substituting Equations 2, 3, and 4 into Equation 5 as shown in Equation 6:

$$C = \frac{<\alpha E_s f(t)>}{1+<\alpha.>+<\frac{d\alpha}{dE}E_s f(t)>}. \quad (6)$$

The value of this compensation electric field can be predicted precisely when the alpha parameter for the ion species, the waveform $f(t)$, and the amplitude of the asymmetric waveform $E_{max}$ are known.

A procedure for extraction of $\alpha(E)$ from experimental measurements of the electric field dependence of the mobility scans is thus known. In this section, some additional considerations regarding the alpha parameter and methods to determine this parameter described. First, emphasis must be given that the alpha parameter is a function (not a number) and the physical and chemical information about an ion is contained in the shape of the $\alpha(E)$ curve. The method of representing this curve is incidental to the topic. The only criterion critical in these methods is that the calculated values for mobility (i.e. $K(E)=K_o\{1+\alpha(E)]\})$ should be as close as possible to the experimental values. The function for $\alpha(E)$ can be represented as an even power series or in complex form. In either instance, the curves of experimental results and calculated should agree closely. Thus, the quality of the approximation is limited by the accuracy of the experimental results and has been illustrated. Discerning the quality of a model based upon two parameters, three parameters, or a nonlinear function with five parameters was difficult. All approximations were located within the error of $\Delta C_1$ (at ±9%).

In this work, a simple uniform method is described to represent the function of $\alpha(E)$, which will be suitable for comparison of results obtained under different experimental conditions. These methods could be used for differing asymmetric waveforms or different designs of IMS drift tubes: linear, cylindrical, or planar FAIMS. In general then, the criteria for choosing the level of approximation of alpha is first to ensure that the method of extracting the alpha parameter uses the least number of individual parameters of the experimental device. Second, the result should contain the fewest number of adjustable parameters, and the approximation curves should be within the experimental error bars. In the next section, the general method to extract the alpha parameter is described and then applied in the subsequent section.

The function of $\alpha(E)$ can be given as a polynomial expansion into a series of electric field strength E degrees as shown in Equation 7:

$$\alpha(E) = \sum_{n=1}^{\infty} \alpha_{2n} \cdot E^{2n} \quad (7)$$

Substituting Equation 7 into Equation 6 provides a value of the compensation voltage as shown in Equation 8 where an uneven polynomial function is divided by an even polynomial function. Therefore an odd degree polynomial is placed after the identity sign to approximate experimental results:

$$C = \frac{\sum_{n=1}^{\infty}\alpha_{2n}S^{2n+1}\langle f^{2n+1}(t)\rangle}{1+\sum_{n=1}^{\infty}(2n+1)\alpha_{2n}S^{2n}\langle f^{2n}(t)\rangle} \equiv \sum_{n=1}^{\infty} c_{2n+1}S^{2n+1}\langle f^{2n+1}\rangle \quad (8)$$

This allows the a comparison of the expected coefficient (approximated) to be compared to the values of alpha parameter as shown in Equation 9:

$$c_{2n+1} = \alpha_{2n}\langle f^{2n+1}\rangle - \sum_{k=1}^{n-1}(2(n-k)+1)c_{2k+1}\alpha_{2(n-k)}\langle f^{2(n-k)}\rangle \quad (9)$$

Alternatively, alpha parameters can be calculated by inverting the formula by using an approximation of the experimental results per Equation 10:

$$\alpha_{2n} = \frac{1}{\langle f^{2n+1}\rangle}\left\{c_{2n+1} + \sum_{k=1}^{n-1}(2(n-k)+1)c_{2k+1}\alpha_{2(n-k)}\langle f^{2(n-k)}\rangle\right\} \quad (10)$$

Any number of polynomial terms (say 2n), in principle, can be determined from Equation 10 though a practical limit exists as the number of polynomial terms in the experimental result of the approximation $c_{2n+1}$ should be higher than the expected number of alpha coefficients $\alpha_{2n}$. Since the size of n depends on the experimental error, the power of the approximation of the experimental curves $C(E_s)$ cannot be increased without limit. Usually N experimental points of $C_i(E_{si})$ exist for the same ion species and experimental data can be approximated by the polynomial using a conventional least-square method. Finally, the number series terms cannot exceed the number of experimental points so increasing the number of series terms above the point where the fitted curves are located within the experimental error bars in unreasonable. In practice, two or three terms are sufficient to provide a good approximation shown in prior findings. The error in measurements must be determined in order to gauge the order of a polynomial for alpha. The sources of error in these experiments (with known on estimated error) were:

1. Error associated with measurement and modeling of the RF-field amplitude (~5%);
2. Error in $C(E_s)$ from a first-order approximation of Equation 4 (~3%), and
3. Error in measuring the compensation voltage (~5–8%).

An approximate error may be ~10% and there is no gain with approximations beyond two polynomial terms; thus, alpha can be expressed as $\alpha(E/N)=1+\alpha_1(E/N)^2+\alpha_2(E/N)^4$ with a level of accuracy as good as permitted by the measurements.

A standard least-square method (regression analysis) was used to approximate or model the experimental findings. For N experimental points with $C_i(E_{si})$ and for $C=c_3S^3+c_5S^5$ a function $y=c_3+c_5x$ can be defined where $y=C/S^3$; $x=S^2$ so $c_5$ and $c_3$ are given by Equations 11 and 12, respectively:

$$c_5 = \frac{\sum_{i=1}^{N} x_i \sum_{i=1}^{N} y_i - N \sum_{i=1}^{N} x_i y_i}{\left(\sum_{i=1}^{N} x_i\right) - N \sum_{i=1}^{N} x_i} \quad (11)$$

$$c_3 = \frac{1}{N}\left(\sum_{i=1}^{N} y_i - c_5 \sum_{i=1}^{N} x_i\right) \quad (12)$$

Through substituting experimental value $c_3$, $c_5$, values for $\alpha_2$ and $\alpha_4$ can be found per Equations 13 and 14:

$$\alpha_2 = c_3 / \langle f^3 \rangle \quad (13)$$

$$\alpha_4 = \frac{c_5 + 3c_3\alpha_2\langle f^2 \rangle}{\langle f^5 \rangle} \quad (14)$$

In order to calculate $\alpha_{2n}$, knowledge is needed for the approximations of experimental curves for $C(E_s)$ and for the function $f(t)$—which is a normalized function describing the asymmetric waveform.

For example, nine data points were identified for each of the eight ketones of FIG. 8, based on the data collected in Table 1 of FIG. 8C. These can be used to compute the α curve for that species, such as with a piecewise linear approximation to the α curve. For example, two data points for butanone are a(Vcomp-a, Vrf-a) and b(Vcomp-b, Vrf-b). Between these two points, the slope and sign of the butanone curve can be computed. More complete characterization of the curve, such as with polynomial curve fitting, is also possible.

Now this data set becomes part of a data store for use in identification of the species of an unknown detected ion species for which two data points are collected and the corresponding curve data is computed. In short, in a simple practice of the invention, we collect data on at least two closely associated points (peaks) for a given ion sample and generate the curve data accordingly. Once we have the detected and computed data, we assume this approximates the alpha curve and therefore do a lookup to our stored data. Upon finding a match, we can then positively identify the sample.

In FIGS. 9A and 9B (monomers and clusters, respectively) we computed unique α curves for ketone ions (acetone, butanone, pentanone, hexanone, heptanone, octanone, nonanone, decanone) based on data collected in the FIG. 7B Table, plotting the percent change in a against the change of field strength for the various data collected ion Table 1 (FIG. 8C). These plots of percent change in α against field strength express a unique signature for each of these ion species. This is loaded in our data store for later comparison: the signature data includes the RF field strength and the compensation voltage at which the peak is detected, we also associate with it the identifying data for the known α function associated with that detected peak location and field conditions for each species.

FIGS. 9A and 9B thus express the α function for individual ketones spanning electric fields of 0 to 80 Td (~23 kV/cm), expressed as a percentage change in alpha as a function of field conditions. These plots are fundamental signature features of these ion species that are independent of the drift tube parameters and can be used in other mobility spectrometers. Thus the α function can be favorably used in practice of the invention to provide a mobility identification data set that is device-independent.

These results are surprising and demonstrate that for chemicals with the same functional group, protonated monomers of a single type exhibit a broad range of behavior vis-à-vis the dependence of coefficients of mobility on electric fields. This difference in behavior for a common moiety suggests that the effect from the electric field must be associated with other aspects of molecular structure. One possible interpretation is that ions are heated during the high field and the effect on the protonated monomer should be striking. These ions with structures of $(H_3O)^+M (H_2O)_n$ or perhaps $(H_3O)^+M (H_2O)_n(N_2)_2$, should be prone to dissociations with slight increases in ion temperature caused by the high field conditions. Thus, ion cross-sections and mobilities would accompany declustered small ions at high fields.

Referring again to FIG. 9A, it will be noted that there is approximately a 20% increase in α(E) for the protonated monomer of acetone with high fields. As the molecular weight of the ketone is increased, ion heating should be less pronounced and reflected in the α(E) function. The α(E) function for proton bound dimers (clusters) is consistent with decreases in mobility under high field conditions. Consequently, the basis for the α(E) function differs from that of protonated monomers. Indeed, the proton bound dimer for decanone undergoes a 5% decrease at high fields. The cause for a decrease in mobility at high fields has no existing model but should be due to increased collisional size or increased strength of interaction between the ion and the supporting gas.

Furthermore, if we were to do the same for the cyclohexane and DMMP in FIG. 1C, the computed alpha curves would differ accordingly. In this manner, we can distinguish ion species even when their mobility curves overlap, as long as we have at least a second detection data set to associate with each detected species in question. Therefore we achieve a high level of assurance for the accuracy of our identifications.

Thus we have shown that the fundamental dependence of mobility for ions in high electric field can be obtained from field asymmetric ion mobility spectrometry. Functions of dependence can be extracted from experiments using known methods to treat imperfect waveforms. These findings show an internal consistency with a homologous series of ketones, and also indicates a mass dependence not previously reported.

Now it will be appreciated that in practice of the invention, ion species are identified based on ion mobility dependence of the species under various field conditions. First, characteristic changes in ion mobility, based on changes in field strength and field compensation, are recorded and stored for a library of known compounds; secondly data is collected for the sample under test for a variety of field conditions; thirdly, a comparison of detection data for the sample under test versus the stored data enables identification of the compounds in the sample. The quality of stored data and strength of the mobility relationship enables improved species identification.

It should be furthermore understood that the invention is applicable not only to one type of field asymmetric ion mobility system but may be applied in general to ion mobility spectrometry devices of various types, including various geometries, ionization arrangements, detector arrangements, and the like, and brings new uses and improved results even as to structures which are all well known in the art. The present invention is not limited to configurations of the examples and may be practiced in any other configurations, including plate-type, planar, radial, spherical, or cylindrical FAIMS devices. Furthermore, in practice of an embodiment of the invention, the output of the FAIMS filter may be detected off board of the apparatus, such as in a mass spectrometer or other detector, and still remains within the spirit and scope of the present invention.

The foregoing discussion has been focused on detection and identification of species of ions. However, this invention is broader and can be applied to any system for identification of unknown species of ions traveling through a varying controlled excitation field, the identification being based on the known characteristic travel behavior of the species under the varying field conditions. The ion or ions to be identified may be traveling alone or in a group of ions of same or differing characteristic travel behavior. The field may be compensated in any of various manners as long as a species of interest is returned to the center of the flow and permitted to pass through the filter while all other species are retarded or neutralized. Identification is made based on known field-dependent differential mobility behavior of at least one species of ions traveling in the field at known field conditions.

E. A Process for Identification of Compounds

Focusing attention now on FIGS. 10A–10F a specific sequence of steps will be described that may be carried out to perform species identification in several of the embodiments of the present invention, which are provided by way of illustration and not limitation. In this illustration, the sequence of steps would be performed by the microprocessor 46 which is associated with the ion mobility spectrometer device 10. As was already described in connection with FIG. 2 there would also be an RF voltage generator 42, compensation voltage generator 44, a memory 47 and an analog to digital converter 48. The microprocessor 46 provides digital control signals to the RF dispersion voltage generator 42 and compensation voltage generator 44 to control the desire drive voltages for the filter 24. These may also include for example, digital to analog converters that are not shown in detail in the drawings here.

The microprocessor 46 coordinates the application of specific RF dispersion voltages Vrf and compensation voltages Vcomp also taking into account the function of observing responses from the detector 26 as read through the analog to digital converter 48. By detecting attributes (such as the peaks) of observed abundances of a particular ion species across a range of Vrf voltages, the microprocessor 46 can thus take steps to identify particular compounds. These may include, for example, comparing or correlating particular "response curve" data against a library of response curve data as stored in the memory 47. They can also include computation of α curve parameters. The results of the comparison operation can be provided in the form of an appropriate output device such as a display or personal computer or the like, or maybe provided by electrical signals through an interface to other data processing equipment.

Figure 10A:
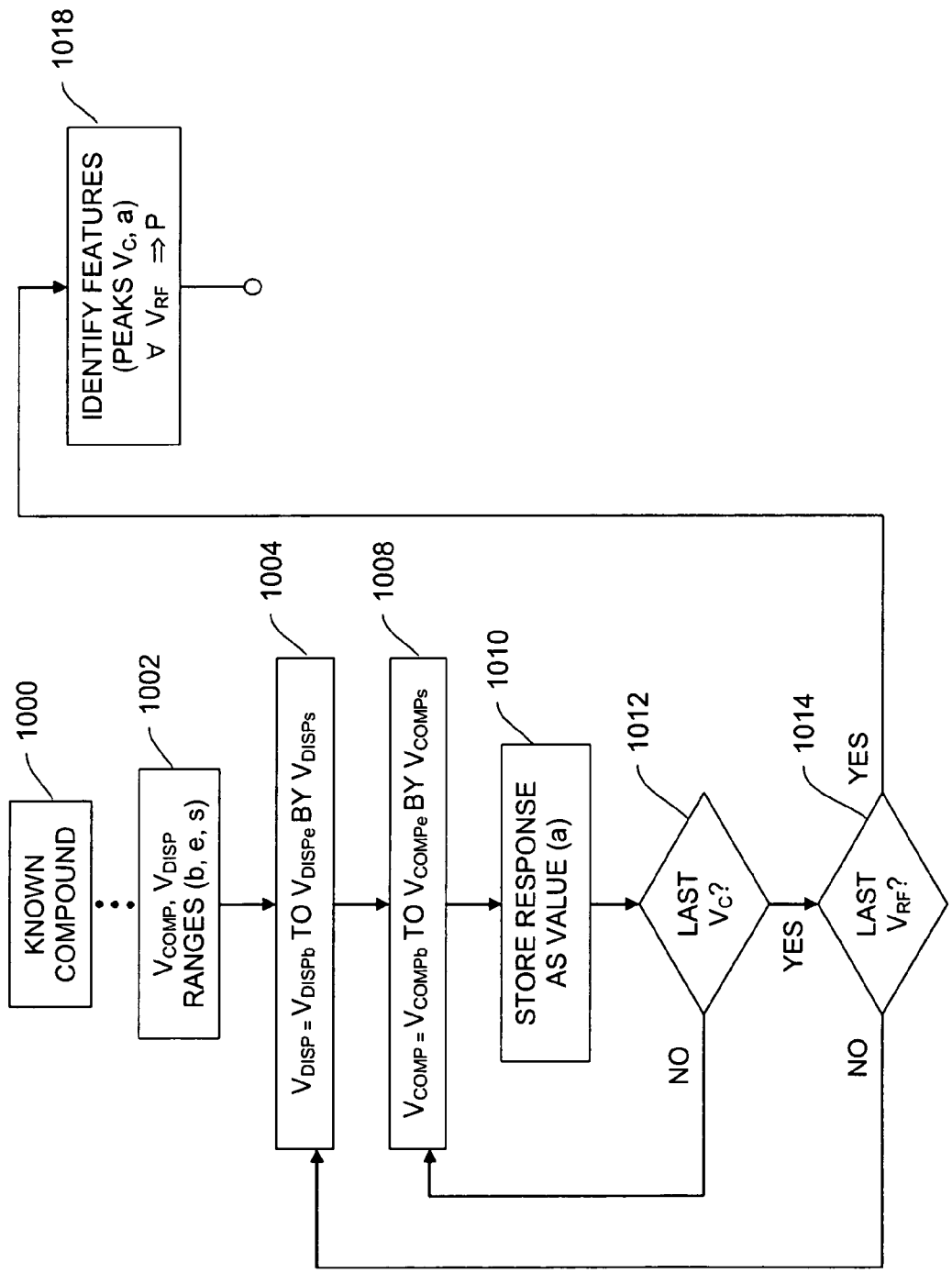
FIG. 10A shows a sequence of steps of a computer process used to acquire data concerning a particular chemical ion species in practice of the present invention.

As shown more particularly in FIG. 10A, a state 1000 is entered into the microprocessor 46 in which a compound is to be analyzed. Here, the compound is known and identified, such as by a user supplying an identifying text string to the computer. A sequence of steps is then performed by which data is to be acquired concerning the known chemical compound. From this state 1000 a next state 1002 is thus entered in which a range of dispersion voltages Vrf and compensation voltages Vcomp are determined by the processor 46. These ranges include a beginning voltage (b) and an end voltage (s) and step voltage(s) to be applied to each of the ranges Vrf is thus varied from an initial value Vrf(b) to a final value Vrf(e) by a step amount Vrf(s). Similarly, Vcomp is to be varied from Vcomp(b) to a final value Vcomp(e) by a step amount Vcomp(s).

The voltage ranges are then applied in the following steps. Specifically, step 1004 is entered in which the Vrf is allowed to step through a range of values. A state 1008 is entered next in which the compensation voltage Vcomp is also swept or stepped through a series of values or ranges.

In state 1010 the response to each applied voltage is stored as a value, a.

If the last compensation voltage has not yet been tested then processing returns to state 1008 in which the next compensation voltage is applied. However, in state 1012 if all of the compensation voltages have been applied then processing proceeds to a state 1014 wherein a test is made to see if all of the dispersion have been applied.

The loop continues until all of the compensation and dispersion voltages have been applied resulting set of data is then analyzed in a state 1018 to identify features of interest. In a specific example being described it will be the peak locations that are of interest. For each such peak in an observed response for a given applied dispersion voltage Vrf, a response value for a specific Vcomp is determined and its corresponding amplitude, a, is detected and stored.

The response curve data, or certain attributes thereof such as the peak locations are then stored as a data object P (or table) as shown in FIG. 10B. Such an object will typically contain an identification of the tested compound such a text string. Also stored of course are a set of the applied dispersion voltages Vrf. For each such dispersion voltage Vrf a corresponding peak compensation voltage is stored. Specifically, what is stored is at least the compensation voltage Vcomp at which a peak was observed, and typically the corresponding amplitude of the response (abundance) observed at that peak.

It is by now understood by the reader that for a given RF voltage Vrf there may actually be a set of compensation voltages at which a number of "peaks" are observed. For example, as was described in connection with FIG. 6A the sample analyzed was made up of a compound of specific ions monomers, cluster ion, and reactant ion peaks. Thus, there should be an accommodation in the structure of object P to anticipate that there will be more than one peak observed in any particular mobility scan, and that the number of peaks per response curve will not always be the same number.

An example data element of object P is thus shown where for a single RF dispersion voltage, Vrf-1, peaks were observed at compensation voltages Vc$1_1$, . . . , Vc$1_n$ having corresponding amplitudes a$1_1$, . . . , a$1_n$. Thus might correspond to the case of the lowest applied dispersion voltage in FIG. 6A, where numerous peaks 601-, 605-1, 608-1 are detected. However, at another dispersion voltage Vrf-m, only a single peak at Vcomp-m, am was detected. This might correspond to a case such as in the uppermost curve of FIG. 6A, where only a single peak 601-m was detected.

In a typical application, a library of data objects P (reference vectors) would be developed by running the steps of FIG. 10A for different known compounds.

Figure 10C:
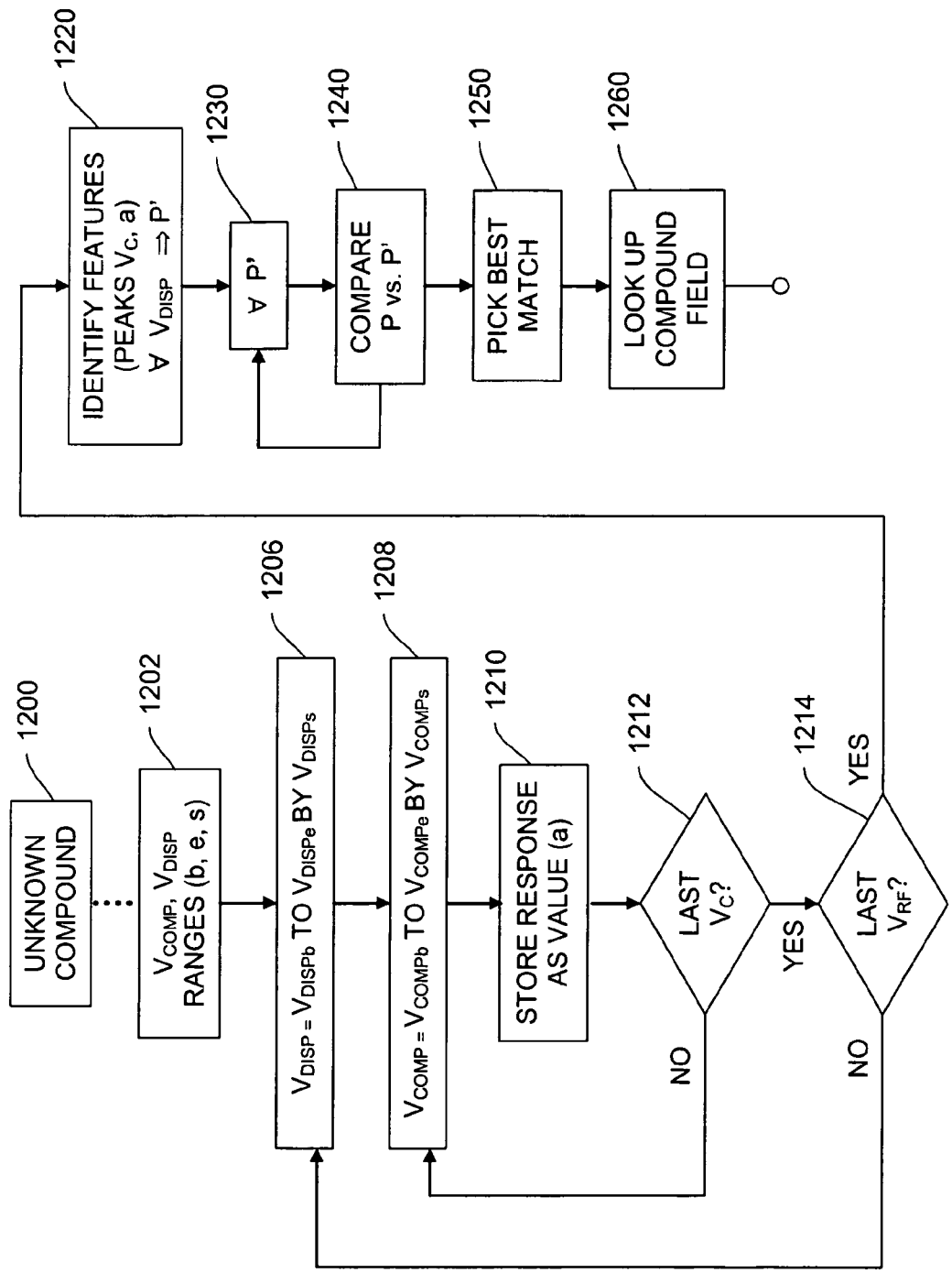
FIG. 10C is a series of steps that may be applied to perform a chemical recognition in practice of the present invention.

This would then permit an instrument to eventually enter a chemical recognition state 1200 as shown in FIG. 10C. From this state a series of measurements are taken in states 1202–1214 that are not unlike the measurements taken in FIG. 10A. Specifically, a series of measurements are taken for a specified compensation and RF voltages. It should be understood that an entire set of all of the same measurements need not be taken in this mode as were taken in the chemical data acquisition mode. Specifically, not all points on a relatively dense response curve need to be taken, only enough to identify each compound.

Once the measurements are taken a state 1220 is entered in which features such as peaks of the response are identified for each peak a corresponding compensation voltage and amplitude may be identified and these stored to a candidate measurement vector P'.

The candidate vector P' thus represents a series of data that need to be tested against a number of candidate compounds. The candidate vector P' is then analyzed in states 1230 and/or 1240 by looking up corresponding counterparts in the library of reference vector objects P, and scoring a match between P and P'. These steps may be iterated until such time as a match or a best match is determined in a state 1250.

It should be understood that any number of techniques may be used to determine a degree of match between P and P'. For example, if the elements (Vcomp, a) of P and P' are considered to be data points in Euclidian geometry space, a distance can be computed. The comparison with the smallest Euclidian distance can then be selected as the best match. However, other recognition techniques may be used or to determine an identify of an unknown compound, for example, are there more sophisticated signal processing techniques such as correlation may be used to resolve peaks; or other known pattern recognition algorithms, neural networks or artificial intelligence techniques may be used to find a best match for P'.

This best match is then identified to a user such as by looking up the compound identifier field and displaying in state 1260.

Figure 10D:
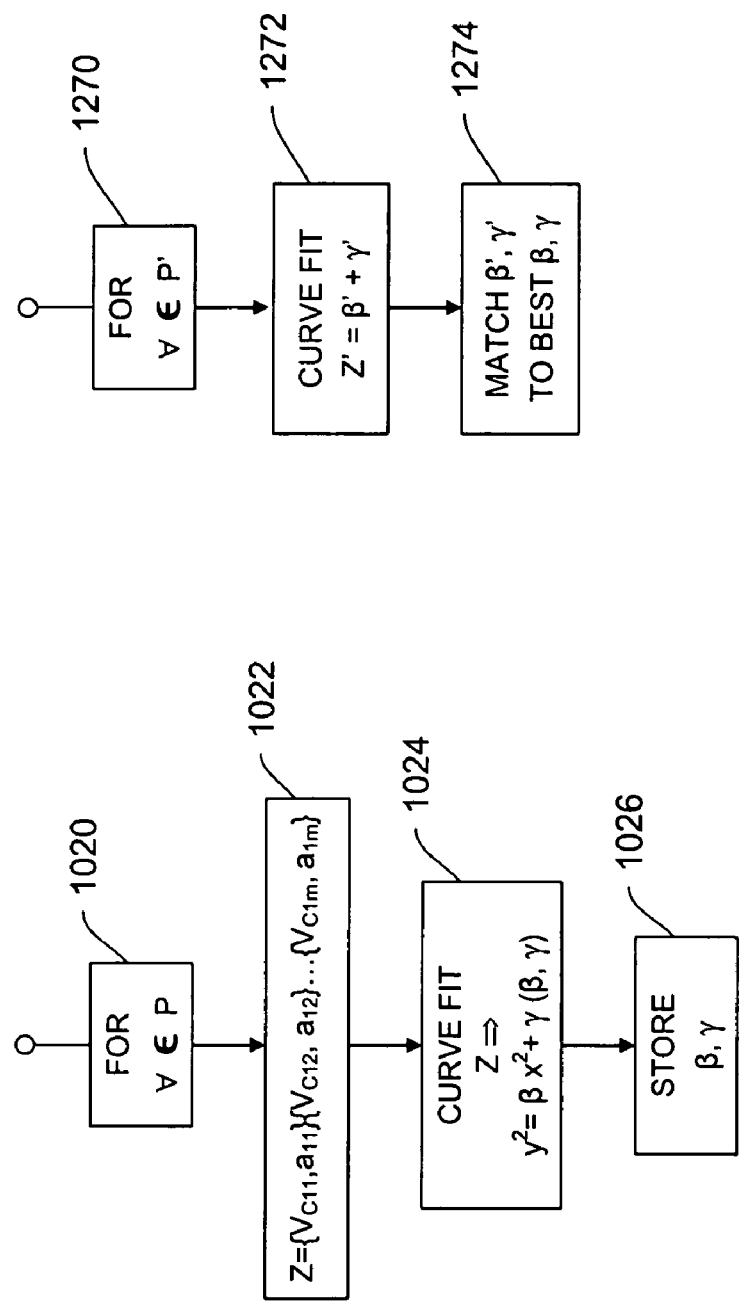
FIG. 10D is a series of steps that may be added to the data acquisition and chemical recognition processes using alpha curve fitting in practice of the present invention.

FIG. 10D shows a series of steps that may be added to the data acquisition phase and the chemical recognition phase to take advantage of second order data processing characteristics. For example, in the data acquisition state, a series of states 1020, 1022, 1024 and 1026 may be added which attempt to curve-fit specific attributes of the measured response. Specifically, a state 1020 may be entered in which for each data element of the object P a vector, z, is formed consisting of the peak compensation voltages vc1, vc12, . . . vc1m.

This vector is in fact a vector of point locations for the peaks observed for a range of compensation voltages. Returning attention to FIG. 6A, briefly, this may correspond to for example locating the points 601-1, . . . 601-m, . . . 601-n corresponding to peak height and locations for the monomer ions of interest. A curve may then be fit through these peaks such as by applying a curve fitting algorithm, in state 1024. In the illustrated example it is assumed that a quadratic equation is fitting the peaks of the form $y^2=\beta x^2+\gamma$. The $\beta$ and $\gamma$ coefficients can then be stored in the state 1026 associated with the vector. The chemical is thus identified by a curve fit to its peak locations approximating its mobility ($\alpha$ coefficient) behavior.

If this is done, a corresponding set of steps 1270, 1272 and 1274 would be typically added to the chemical recognition process. Thus, peaks would be identified instead of comparing raw data values in states 1270 and 1272 by performing a curve fit to observe data and then determining $\gamma$ and $\beta$ coefficients. In state 1274 the $\beta$ and $\gamma$ coefficients would be tested to determine closest matches in the P object library.

Figure 10E:
FIG. 10E is a diagram of a more complex data structure that can be used in practice of the present invention.
Figure 10F:
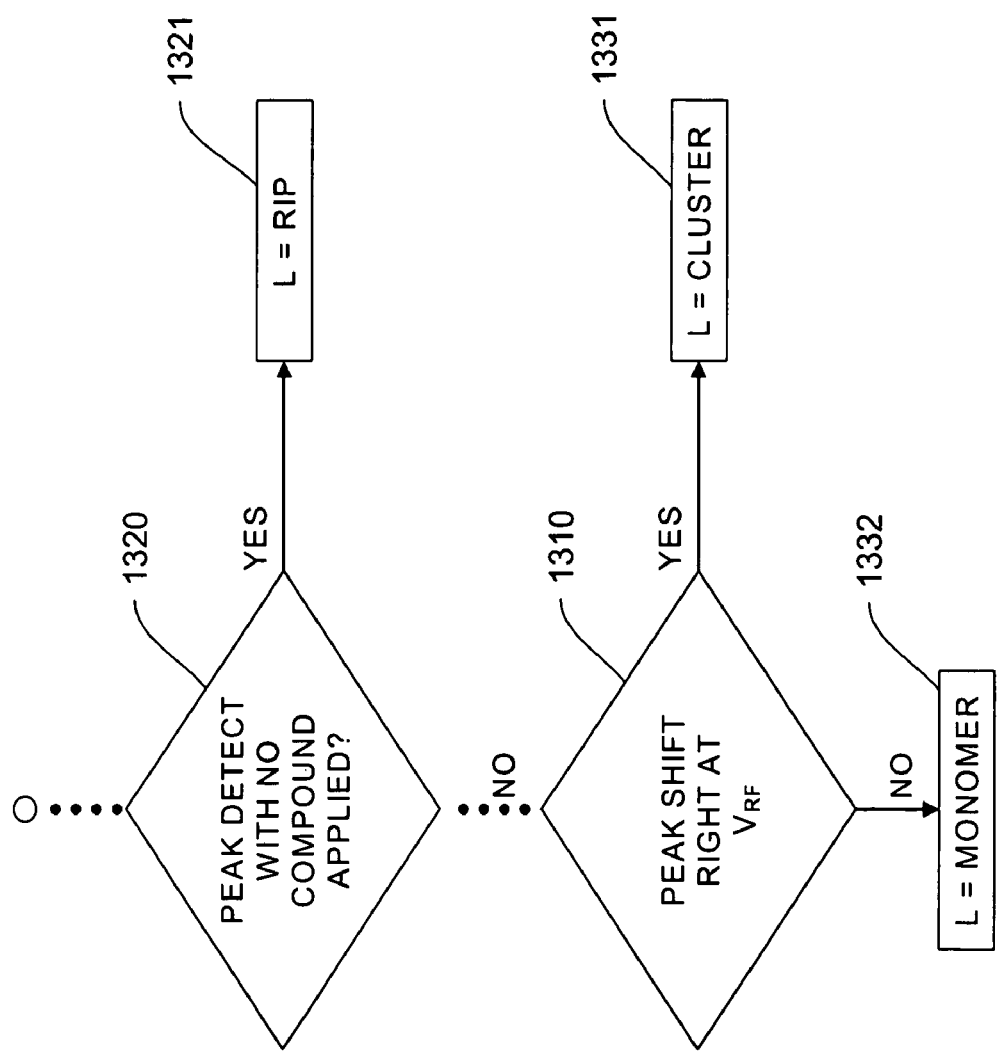
FIG. 10F is a sequence of processes that may be used to distinguish monomer and cluster peak responses in practice of the present invention.

FIG. 10F shows a series of steps that may be used to identify or distinguish peaks in the acquisition phase. Here initial data may be added to the objects P by identifying peaks as a cluster peak or monomer peak. Specifically, if a peak shift is observed as a range as a range of field condition voltages (e.g., Fog. 6A) is increased then this might be identified as a cluster peak. If the peak does not meet specific shifting criteria it might be identified as a monomer peak. States 1310, 1331, and 132 could thus be added to the identification process. The results of these steps would add an additional parameter L associated with each data point in the object P to further identify each peak as a monomer cluster or other peak type, as shown in FIG. 1E.

Other approaches to this could potentially be used to label peaks. For example reactant ion peaks could also be identified by running an analysis on a response of the instrument when no sample is applied. In this mode only the reactant ion peaks would occur in their behavior across a range of compensation voltages could be stored. In any event, information concerning the particular type of peak can thus be stored in the pointer data in a state 1320 at which such a peak is detected. This information can then be added to the objects P specifically as shown in FIG. 10E.

Figure 10G:
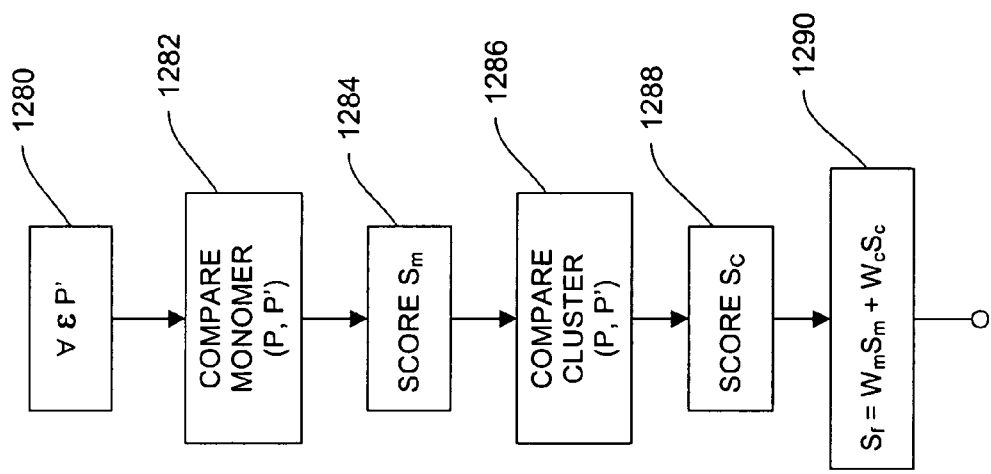
FIG. 10G is a diagram of a process showing how monomer and cluster scores may be combined in practice of the present invention.

FIG. 10G shows additional processing steps that might be performed in the chemical recognition state to take advantage of the situation of FIGS. 8A and 8B in which monomer and cluster ion behavior is observed. Specifically, these steps in FIG. 10G might be added as further steps 1280 in the recognition phase. Here for every candidate peak P' corresponding monomer peak in the reference array P is compared. A score is then associated with the closest of the match in state 1284 similarly in state 1286 a cluster peak may be compared with its corresponding in the peak library P. A score sc is then determined in step 1288 depending on the closest of this match. Finally, in a state 1290 a final score sf can be associated with weighting the monomer peak score and the cluster peak score by weighting factors wm and wc for example in an instance where cluster peaks are expected to provide more information than monomer peaks, cluster peaks might be weighted highly and monomer peaks relatively low or zero factor. This weighting is understood now how both monomer and cluster peak identification can be combined to further refine compound identification.

It will be evident to one skilled in the art that various modifications and variations may be made to the present invention without departing from the spirit and scope herein. For example, although the apparatus illustrated in FIG. 2 has a single filter 24 and detector 28, it should be understood that a series of filters 24 can be applied to a specific gas ionized sample S. The first can be used as a pre-filter to limit chemical species to a particular range of species that are know to be of interest, with the second filter in the series being used to provide for detailed sweeping at precise incrementing voltages to provide for greater resolution.

In a further embodiment of the invention we are able to separate and distinguish between overlapping FAIMS spectra, with improved species identification. Turning to FIG. 11A, we show two overlapping spectra for species A and species B, showing the change in mobility ($\Delta k$) as a function of electric field (E). These spectra are essentially overlapping. This may occur when two species are detected that have identical or very similar high field mobility characteristics.

It will be further appreciated that whle DMS devices have good range and species resolution, this is not true for every ion species. Species in a particular frequency range, say 1–2 MHz may be difficult to resolve for a given system, say for molecules having weights of 300–700 AMU. These ions tend to pass very close (i.e., have compensation voltage values very close) to zero compensation. But by selectively passing ions with such compensation level through the DMS as a pre-filter and introducing them into the IMS, these ions species can be resolved with added IMS detection data. This technique can also be applied to separation and identification of dimers, clusters and the like.

Now this IMS data can be used to identify the ion species or can be added to DMS detection data to further improve species identification. This works for species that have similar high field spectra because it is likely or at least possible that the low field characteristics (based on the low field coefficient Ko) of species will be different. We therefore obtain the low field detection data for overlapping species and then add this data to separate their spectra.

The low field data is essentially represented as a dc level. For example, species A might have a characteristic low field mobility represented as dc value of −1 and species B might have a characteristic low field mobility represented as dc value −2. Now each low field mobility parameter can be added to the detection data for that species as a dc-offset. FIG. 11B shows where the spectra A, B are each offset by an amount equivalent to their own associated dc-offset, resulting in spectra separation.

It is therefore a method of an embodiment of the present invention as described above to detect both species-specific low field mobility (Ko) and high field mobility (ΔK) differences and to use this data to provide detection spectra with a high degree of species discrimination. We can determine the parameters of K(E) by various means. For example, it is possible to extract low field mobility by processing of DMS detection spectra and then to add this to the DMS spectra as an offset to further separate overlapping spectra.

It is also possible to obtain low field mobility data directly from an IMS spectrometer for a given sample under test and to add this IMS low field mobility data to the DMS spectra to obtain the improved detection result of FIG. 11B. This process combines the detection data normally associated with IMS with the detection data normally associated with DMS with improved detection results. Now detection spectra may more completely represent the effect of the electric field, K(E), where the K(o) low voltage coefficient of mobility is obtaining in any manner, and the high field differential mobility is obtained from the DMS.

Therefore use of IMS low field detection data with high field DMS spectra data has several advantages. Further provision of an integrated IMS/DMS system has several additional benefits as shown below. In a preferred embodiment, this is achieved wherein the DMS is a pre-filter to an IMS.

In conventional time of flight (TOF) IMS, ionized sample is held at gate and then released into a drift tube. The ions are conveyed down the drift tube based on their mobility in a dc gradient between the shutter and an attractor electrode. The time of drift to the collector electrode is related to the low field mobility of the detected ion species. However, the shutter mechanism, whether by field or mechanical, can be complicated.

In one series of embodiments of the invention, DMS and IMS are combined, wherein their detection data are harnessed to provide improved species discrimination. In one approach, a DMS device, whether plate-type, cylindrical, radial, or otherwise, filters an ionized sample flow preferably according to the improved field asymmetric ion mobility practices of the invention. The filtered stream passing out of the DMS filter has been reduced down to an ion species, or perhaps one set of species have overlapping spectra, based on high field mobility differences. In further embodiment, this pre-filtered ion flow is further analyzed in a IMS device.

Figures 12A, 12B:
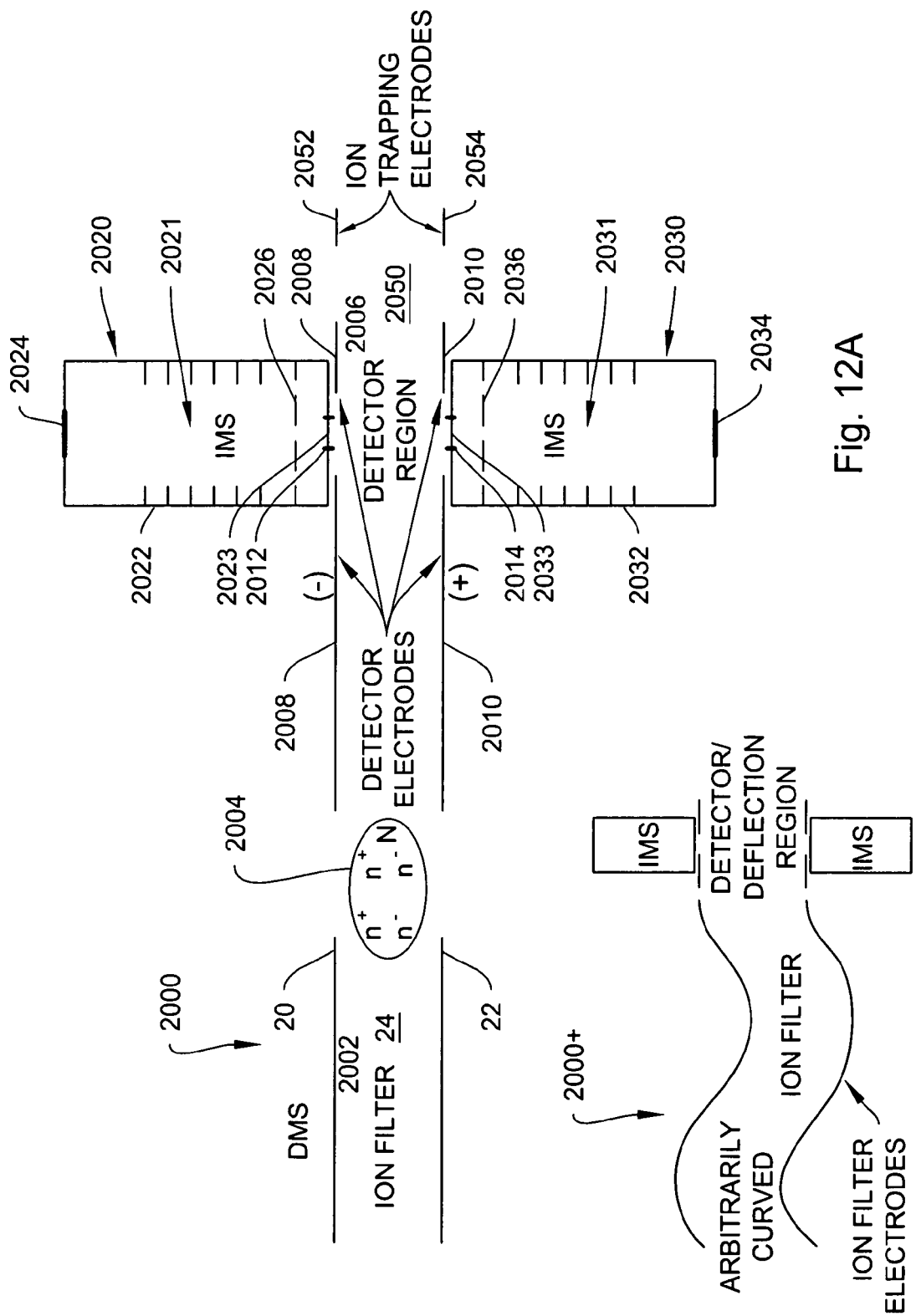
FIG. 12A, 12B show DMS-IMS embodiments of the invention.

An illustrative embodiment of the invention is shown in FIG. 12A, wherein a DMS ion filter 2000 (such system 10 shown in FIG. 2,) is modified to accommodate improved spectral separation. The ion filter region 2002 is the same as earlier described, having ion filter 24 with ion filter electrodes 20, 22. Filtering preferably proceeds based on differences in ion mobility in the filter field and thereafter the filtered ion flow 2004 exiting the filter enters detector region 2006.

Detector region 2006, includes detector electrodes 2008, 2010. Now, as before, two species of ions 17+ and 17−, can be passed by the ion filter and can enter the detection region where further separation occurs followed by species detection and identification.

As noted in regard to FIG. 2, detector 26 includes a first detector electrode 28 and a second detector electrode 30. These electrodes may be biased to detect either negative or positive species. But electrode 28 may be positively biased to attract ion 17− and to repels ion 17+, while electrode 30 may be biased negatively to attract ions 17+ while repelling ions 17−. It is a feature of this invention that where these electrodes are oppositely biased they may make simultaneous detections of positive and negative spectra.

It will be further appreciated that the separated ions deposit their charges on the appropriately biased detector electrodes 28 or 30. The signals generated by the ions collecting at detector electrodes 28 and 30 are amplified by respective amplifiers 36 and 38 to provide signals to command and control unit 34.

In a further embodiment of the invention, a combined DMS with shutterless IMS detector system is provided. This arrangement may be used to selectively inject particular pre-filtered ion species into an IMS that has been tuned to a specific range or polarity.

As shown in FIG. 12A, detector electrodes 2008 and 2010 are provided to perform the function of detector electrodes 28 and 30 of FIG. 2. However, an orifice 2012 is formed in electrode 2008 and an orifice 2014 is formed in electrode 2010. Now at least one IMS device, preferably two, devices are formed as part of apparatus 2000.

As shown in FIG. 12A, each IMS section includes a drift tube 2021, 2031, flow gradient electrodes 2022, 2032, an orifice 2023, 2033 for mating with orifice 2012, 2014, such that IMS section 2020 is in fluid communication with orifice 2012 and IMS section 2030 is in fluid communication with orifice 2014. The IMS sections also include attractor electrodes, 2024, 2034.

In a first mode of operation, as with the ion flow of FIG. 2, the separated ions 17+, 17− deposit their charges on the appropriately biased detector electrodes 2008, 2010, wherein positive and negative ions are deflected to the oppositely charged detector electrodes, assuming that the IMS sections are not charged. Assuming that electrode 2008 is negatively charged and electrode 2010 is positively charged, then ions 17+ will be driven toward electrode 2008 for detection and ions 17− will be drive toward electrodes 2010 for detection. These ions are detected when they deposit their charges on the appropriate electrode.

This deposit process is changed however when the IMS sections are enabled. A strong charge is placed on the attractor electrodes 2024, 2034 so as to draw some or all of the ions headed to the local detector electrode 2008, 2010 into the IMS drift tube 2021, 2031. For example, with detector electrode 2008 mildly negatively biased and attractor electrode 2024 being more negatively biased, the ion flow splits with some ions 17+ contacting electrode 2008 for generating DMS detection data and some ions flowing into the drift tube 2021.

The ions in the drift tube are propelled by a DC gradient established at electrodes 2022, culminating with the ions driving into the more negatively charged attractor electrode 2024 (which also serves as a collector or detector electrode). These ion strikes are detected and are provided as IMS time-of-flight detection data which can be correlated with lookup tables of known species behavior.

But in a further embodiment of the invention, the DMS and IMS detection data are combined to provide improved species spectra separation and identification. Now the DMS curve is anchored by addition of a dc offset from the IMS data that is characteristic of the species being analyzed. To wit: the absolute mobility information associated with that detected ion species obtained by measuring the low field mobility value for that species is combined with the differential mobility data for that species. This anchors the mobility curve and results in a precise fingerprint for that species.

It will be further appreciated that in practice of the invention, it is possible to provide positive and negative ion species separation and detection simultaneously within the DMS apparatus and then simultaneously in both IMS detectors. It will therefore be further appreciated that this compact apparatus can process complex samples in real time with very useful species detections.

These above illustrative embodiments can be achieved by use of conventional IMS devices attached to the orifices 2012, 2014. However, the embodiment of FIG. 12A may be provided in a compact and integrated package. Such package may also include a shutterless IMS as described or optionally a more conventional IMS configuration having a control gate 2026, 2036 in the drift tube as shown by dotted line in the figure.

FIG. 12B shows non-flat or non-straight flow path/electrodes which may be incorporated into apparatus 2000. It will be further appreciated that the embodiment of FIG. 12 or similar arrangements may be provided in a variety of configuration which may include combined series and/or parallel DMS-IMS.

In yet a further embodiment of the invention of FIG. 12A, an ion trap 2050 is defined which generates an electric field between electrodes 2052, 2054 to drive hold positive or negative ions in the region of the detector. This enables buildup of the sample which then is released into the IMS as in the conventional shuttered IMS system.

Various illustrative examples of novel detection strategies in practice of embodiments of the invention are disclosed herein. This discussion may be applied to ions, particles, articles, biologicals, vehicles, people, things, or the like, and variations thereof; these also may be described by alternative terms, such as "ions", without limitation, and yet such breadth will be understood to be within the spirit and scope of the present invention.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for identification of an unknown item in a sample traveling through an excitation field, the excitation field having a varying influence upon the mobility behavior of the sample traveling the excitation field, the method comprising the steps of:

generating a varying excitation field;

subjecting a sample to the excitation field, the sample having field-dependent mobility behavior that reflects field conditions, and the excitation field having sufficient strength to fragment the sample;

subjecting the sample to a plurality of field conditions in the excitation field;

compensating the plurality of field conditions to pass the unknown item through the excitation field; and identifying the unknown item as a member of a known species, the identification being based on known field-dependent mobility behavior of the known species in the plurality of compensated field conditions.

2. A method as in claim 1 wherein the fragmenting produces positive and negative ions.

3. A method as in claim 2 comprising identifying the positive and negative ions over a rage of compensation voltages.

4. A method as in claim 1 comprising varying the excitation field to produce ionized monomers.

5. A method as in claim 1 wherein the plurality of field conditions are varied over a range of dispersion voltages to produce multiple attributes of the field-dependent mobility behavior dependent on compensation voltage.

6. A method as in claim 5 wherein the multiple attributes are peaks, and each of the peaks identifies a particular ion.

* * * * *

UNITED STATES PATENT AND TRADEMARK OFFICE
CERTIFICATE OF CORRECTION

| | | |
|---|---|---|
| PATENT NO. | : 7,119,328 B2 | Page 1 of 1 |
| APPLICATION NO. | : 10/738967 | |
| DATED | : October 10, 2006 | |
| INVENTOR(S) | : Kaufman et al. | |

It is certified that error appears in the above-identified patent and that said Letters Patent is hereby corrected as shown below:

In claim 1, column 36, line 19, insert --through-- after "traveling"

Signed and Sealed this

Second Day of January, 2007

JON W. DUDAS
*Director of the United States Patent and Trademark Office*